United States Patent
Ravikumar et al.

(10) Patent No.: US 7,348,391 B2
(45) Date of Patent: Mar. 25, 2008

(54) POLYMERIC BEADS FOR OLIGOMER SYNTHESIS

(75) Inventors: Vasulinga Ravikumar, Carlsbad, CA (US); Raju K. Kumar, San Marcos, CA (US); Kenjirou Mori, Osaka (JP); Tatsuya Konishi, Osaka (JP); Ayako Matsunawa, Tokyo (JP); Takeo Matsumura, Miyagi (JP); Cheiko Kitaura, Osaka (JP); Gang Zhao, Oceanside, CA (US)

(73) Assignees: Isis Pharmaceuticals, Inc., Carlsbad, CA (US); Nitto Denko Corporation (JP)

( * ) Notice: Subject to any disclaimer, the term of this patent is extended or adjusted under 35 U.S.C. 154(b) by 139 days.

(21) Appl. No.: 11/218,875

(22) Filed: Sep. 2, 2005

(65) Prior Publication Data

US 2006/0051800 A1    Mar. 9, 2006

Related U.S. Application Data

(60) Provisional application No. 60/606,873, filed on Sep. 2, 2004.

(51) Int. Cl.
*C08F 12/34*    (2006.01)
*C08F 136/00*    (2006.01)
*C08F 212/06*    (2006.01)
*C07F 112/06*    (2006.01)
*C07H 21/00*    (2006.01)

(52) U.S. Cl. .................. 526/336; 526/340.1; 526/347; 526/341.1; 536/25.3; 536/25.33; 536/25.34

(58) Field of Classification Search .............. 536/25.3, 536/25.33, 25.34

See application file for complete search history.

(56) References Cited

U.S. PATENT DOCUMENTS

| | | |
|---|---|---|
| 4,908,405 A | 3/1990 | Bayer et al. |
| RE34,069 E | 9/1992 | Koster et al. |
| 5,262,530 A | 11/1993 | Andrus et al. |
| 5,391,667 A | 2/1995 | Dellinger |
| 5,750,666 A | 5/1998 | Caruthers et al. |
| 5,889,136 A | 3/1999 | Scaringe et al. |
| 6,008,400 A | 12/1999 | Scaringe et al. |
| 6,043,353 A | 3/2000 | Pon et al. |
| 6,111,086 A | 8/2000 | Scaringe |
| 6,300,486 B1 | 10/2001 | Froehler et al. |
| 6,335,438 B1 | 1/2002 | Fonnum |
| 2002/0045266 A1 | 4/2002 | Fenniri |
| 2005/0054742 A1 | 3/2005 | Mori et al. |
| 2005/0256285 A1 | 11/2005 | Mori et al. |
| 2006/0051800 A1* | 3/2006 | Ravikumar et al. ............ 435/6 |

FOREIGN PATENT DOCUMENTS

EP    0289029 B1    7/1996

OTHER PUBLICATIONS

PCT International Search Report for PCT/US2005/031425 dated Apr. 28, 2006.

* cited by examiner

*Primary Examiner*—L. E. Crane
(74) *Attorney, Agent, or Firm*—Isis Patent Department

(57) ABSTRACT

The present invention provides solid support media for use in oligomer synthesis, methods of producing the media, and methods of using the media. In some embodiments, the processes of the invention comprise (a) providing an organic phase comprising an olefin monomer, a cross-linker, a functionalizing reagent and an initiator; and (b) contacting the organic phase with an aqueous phase under conditions of time and temperature effective to form the polymeric bead.

25 Claims, No Drawings

POLYMERIC BEADS FOR OLIGOMER SYNTHESIS

CROSS REFERENCE TO RELATED APPLICATION

This application claims benefit of U.S. Provisional Application No. 60/606,873 filed Sep. 2, 2004. The entire disclosure of this application is incorporated herein by reference.

FIELD OF THE INVENTION

The present invention relates to solid support media for use in oligomer synthesis, to methods of producing the media, and to methods of using the media.

BACKGROUND OF THE INVENTION

Solid state synthesis is applicable to the preparation of a wide variety of polymeric compounds such as nucleobase-containing polymers (for example oligonucleotides and their analogs), amino acid containing polymers (for example proteins, peptides, and their analogs). Solid state synthesis also is applicable to the preparation of compounds by combinatorial methods.

Oligonucleotides have been used in various biological and biochemical applications. They have been used as primers and probes for the polymerase chain reaction (PCR), as antisense agents used in target validation, drug discovery and development, as ribozymes, as aptamers, and as general stimulators of the immune system. As the popularity of oligonucleotides has increased, the need for producing greater sized batches, and greater numbers of small-sized batches, has increased at pace. Additionally, there has been an increasing emphasis on reducing the costs of oligonucleotide synthesis, and on improving the purity and increasing the yield of oligonucleotide products.

A number of innovations have been introduced to the art of oligonucleotide synthesis. Amongst these innovations has been the development of excellent orthogonal protecting groups, activators, reagents and synthetic conditions. The oligonucleotides themselves have been subject to a variety of modifications and improvements. Amongst these are chemistries that improve the affinity of an oligonucleotide for a specific target, that improve the stability of an oligonucleotide in vivo, that enhance the pharmacokinetic (PK) and toxicological (Tox) properties of an oligonucleotide, etc. These novel chemistries generally involve a chemical modification to one or more of the constituent parts of the oligonucleotide.

The term "oligonucleotide" thus embraces a class of compounds that include naturally-occurring, as well as modified, oligonucleotides. Both naturally-occurring and modified oligonucleotides have proven useful in a variety of settings, and both may be made by similar processes, with appropriate modifications made to account for the specific modifications adopted. A naturally occurring oligonucleotide, i.e. a short strand of DNA or RNA may be envisioned as being a member of the following generic formulas, denominated oligo-RNA and oligo-DNA, respectively, below:

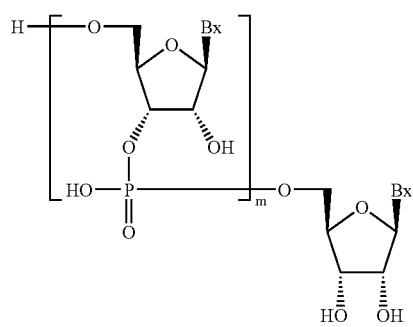

oligo-RNA

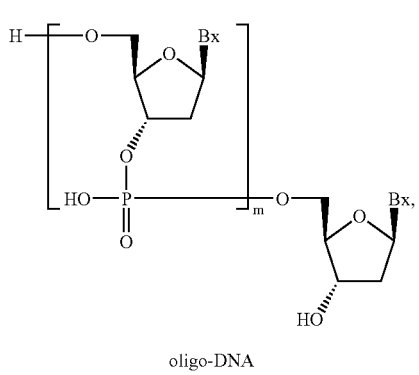

oligo-DNA wherein m is an integer of from 1 to about 100, and Bx is one of the naturally occurring nucleobases.

Physiologic pH, an oligonucleotide occurs as the anion, as the phosphate easily dissociates at neutral pH, and an oligonucleotide will generally occur in solid phase, whether amorphous or crystalline, as a salt. Thus, unless otherwise modified, the term "oligonucleotide" encompasses each of the anionic, salt and free acid forms above.

In essence, a naturally occurring oligonucleotide may be thought of as being an oligomer of m monomeric subunits represented by the following nucleotides:

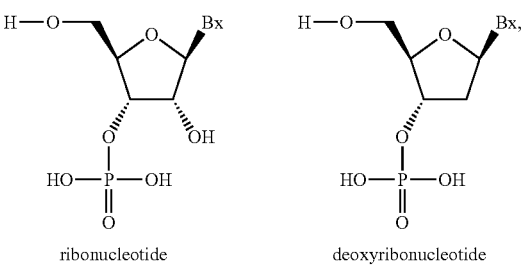

ribonucleotide          deoxyribonucleotide wherein each Bx is a nucleobase, wherein the last residue is a nucleoside (i.e. a nucleotide without the 3'-phosphate group).

As mentioned above, various chemistry modifications have been made to oligonucleotides, in order to improve their affinity, stability, PK, Tox, and other properties. In general, the term oligonucleotide, as now used in the art, encompasses inter alia compounds of the formula:

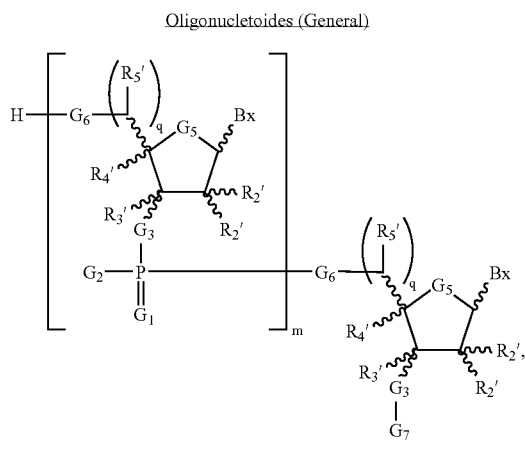

Oligonucletoides (General)

wherein m is an integer from 1 to about 100, each $G_1$ is O or S, each $G_2$ is OH or SH, each $G_3$ is O, S, $CH_2$, or NH, each $G_5$ is a divalent moiety such as O, S, $CH_2$, CFH, $CF_2$, —CH=CH—, etc., each $R_2'$ is H, OH, O-rg, wherein rg is a removable protecting group, a 2'-substituent, or together with $R_4'$ forms a bridge, each $R_3'$ is H, a substituent, or together with $R_4'$ forms a bridge, each $R_4'$ is H, a substituent, together with $R_2'$ forms a bridge, together with $R_3'$ forms a bridge, or together with $R_5'$ forms a bridge, each q is 0 or 1, each $R_5'$ is H, a substituent, or together with $R_4'$ forms a bridge, each $G_6$ is O, S, $CH_2$ or NH, and each $G_7$ is H, $PO_3H_2$, or a conjugate group, and each Bx is a nucleobase, as described herein (i.e. naturally occurring or modified).

The standard synthetic methods for oligonucleotides include the solid phase methods first described by Caruthers et al. (See, for example, U.S. Pat. No. 5,750,666, incorporated herein by reference, especially columns 3-58, wherein starting materials and general methods of making oligonucleotides, and especially phosphorothioate oligonucleotides, are disclosed, which parts are specifically incorporated herein by reference.) These methods were later improved upon by Köster et al. (See, for example, U.S. Pat. No. RE 34,069, which is incorporated herein by reference, especially columns, wherein are disclosed, which parts are specifically incorporated herein by reference.) These methods have further been improved upon by various inventors, as discussed in more detail below. Methods of synthesizing RNA are disclosed in, inter alia, U.S. Pat. Nos. 6,111,086, 6,008,400, and 5,889,136, each of which is incorporated herein in its entirety. Especially relevant are columns 7-20 of U.S. Pat. No. 6,008,400, which are expressly incorporated herein by reference.

The general process for manufacture of an oligonucleotide by the Köster et al. method may be described as follows:

First, a synthesis support is prepared by covalently linking a suitable nucleoside to a solid support medium (SS) through a linker. Such a synthesis support is as follows:

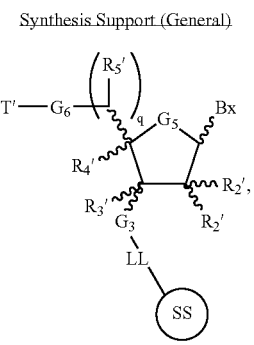

Synthesis Support (General)

wherein SS is the solid support medium, LL is a linking group that links the nucleoside to the support via $G_3$. The linking group is generally a di-functional group, which covalently binds the ultimate 3'-nucleoside (and thus the nascent oligonucleotide) to the solid support medium during synthesis, but which is cleaved under conditions orthogonal to the conditions under which the 5'-protecting group, and if applicable any 2'-protecting group, are removed. T' is a removable protecting group, and the remaining variables have already been defined, and are described in more detail herein. Suitable synthesis supports may be acquired from Amersham Biosciences under the brand name Primer Support 200™. The solid support medium having the synthesis support attached thereto may then be swelled in a suitable solvent, e.g. acetonitrile, and introduced into a column of a suitable solid phase synthesis instrument, such as one of the synthesizers available form Amersham Biosciences, such as an ÄKTAoligopilot™, or OligoProcess™ brand DNA/RNA synthesizer.

In the foregoing method, synthesis is carried out from 3'- to 5'-end of the oligomer. In each cycle, the following steps are carried out: (1) removal of T', (2) coupling, (3) oxidation, (4) capping. Each of the steps (1)-(4) may be, and generally is, followed by one or more wash steps, whereby a clean solvent is introduced to the column to wash soluble materials from the column, push reagents and/or activators through the column, or both. The steps (1)-(4) are depicted below:

Oligo Synthesis Cycle-Step 1

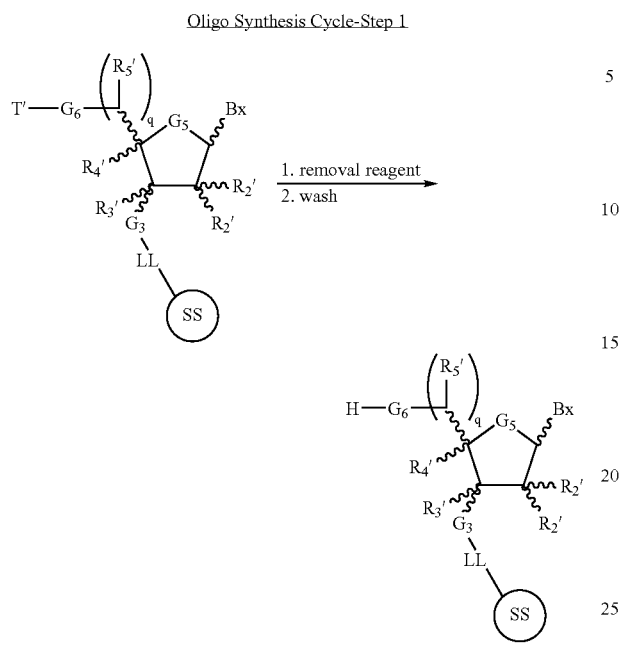

In general, T' is selected to be removable under conditions orthogonal to those used to cleave the oligonucleotide from the solid support medium at the end of synthesis, as well as those used to remove other protecting groups used during synthesis. An art-recognized protecting group for oligonucleotide synthesis is DMT (4,4'-dimethoxytrityl). The DMT group is especially useful as it is removable under weakly acid conditions. Thus, an acceptable removal reagent is 3% DCA in a suitable solvent, such as acetonitrile. The wash solvent, if used, may conveniently be acetonitrile.

The support typically is a controlled pore glass or a polymeric bead support. Some polymeric supports are disclosed in the following patents: U.S. Pat. No. 6,016,895; U.S. Pat. No. 6,043,353; U.S. Pat. No. 5,391,667 and U.S. Pat. No. 6,300,486, each of which is specifically incorporated herein by reference.

After removal of protecting group T', the next step of the synthetic cycle is the coupling of the next nucleoside synthon. This is accomplished by reacting the deprotected support bound nucleoside with a nucleoside phosphoramidite, in the presence of an activator, as shown below:

Oligo Synthesis Cycle-Step 2

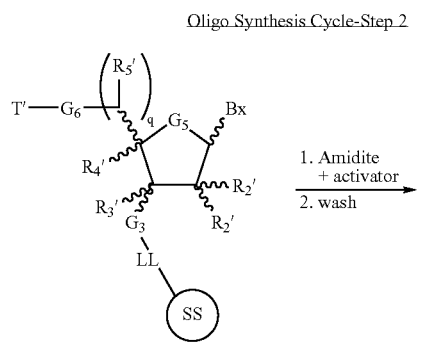

-continued

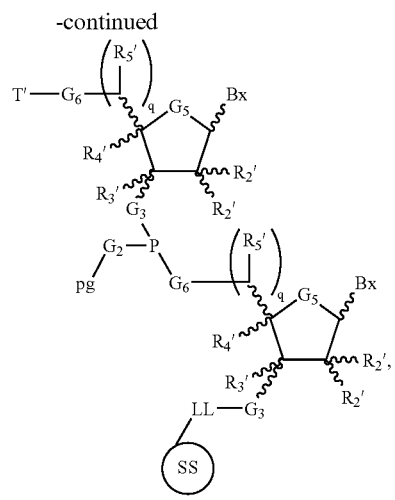

The amidite has the structure:

Amidite (General)

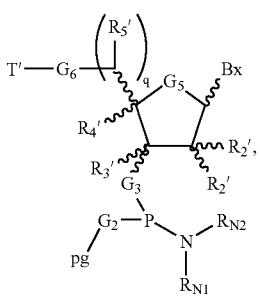

wherein pg is a phosphorus protecting group, such as a cyanoethyl group, and $NR_{N1}R_{N2}$ is an amine leaving group, such as diisopropyl amino. See, Köster et al., supra, for information on manufacturing of the amidite. Typically used activators include for example tetrazole, dicyano imidazole, or pyridinium salts. Other suitable amidites, and methods of manufacturing amidites, are set forth in the following patents: U.S. Pat. No. 6,133,438; U.S. Pat. No. 5,646,265; U.S. Pat. No. 6,124,450; U.S. Pat. No. 5,847,106; U.S. Pat. No. 6,001,982; U.S. Pat. No. 5,705,621; U.S. Pat. No. 5,955,600; U.S. Pat. No. 6,160,152; U.S. Pat. No. 6,335,439; U.S. Pat. No. 6,274,725; U.S. Pat. No. 6,329,519, each of which is specifically incorporated herein by reference, especially as they relate to manufacture of amidites. Suitable activators are set forth in the Caruther et al. patent and in the Köster et al. patent. Especially suitable activators are set forth in the following patents: U.S. Pat. No. 6,031,092 and U.S. Pat. No. 6,476,216, each of which is expressly incorporated herein by reference.

The next step of the synthesis cycle is oxidation, which indicates that the P(III) species is oxidized to a P(V) oxidation state with a suitable oxidant:

Oligo Synthesis Cycle-Step 3

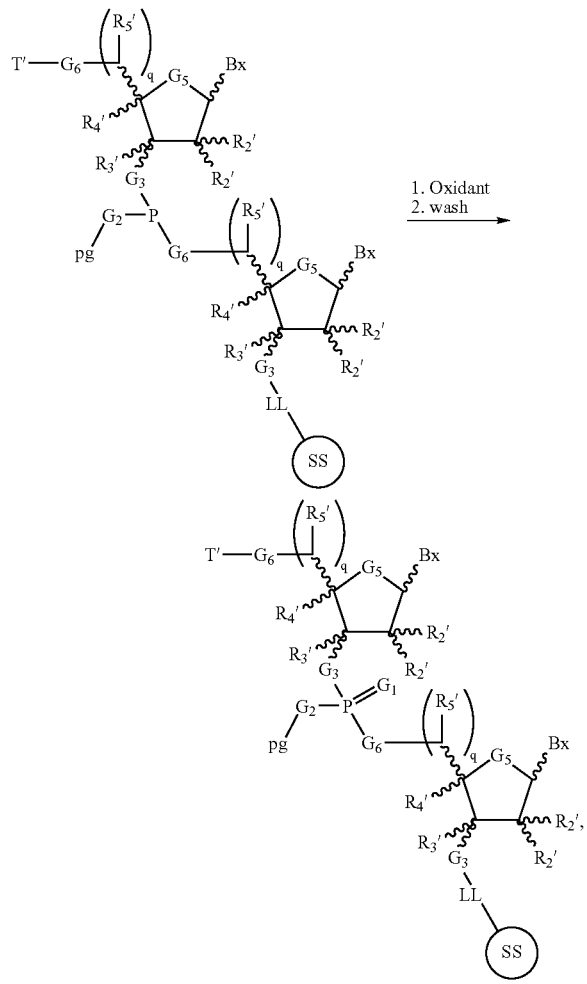

wherein $G_1$ is O or S.

The oxidant is an oxidizing agent suitable for introducing $G_1$. In the case where $G_1$ is oxygen, a suitable oxidant is set forth in the Caruthers et al. patent, above. In cases where $G_2$ is sulfur, the oxidant may also be referred to as a thiation agent or a sulfur-transfer reagent. Suitable thiation agents include the so-called Beaucage reagent, 3H-1,2-benzothiol, phenylacetyl disulfide (also referred to as PADS; see, for example the patents: U.S. Pat. Nos. 6,114,519 and 6,242,591, each of which is incorporated herein by reference) and thiouram disulfides (e.g. N,N,N',N'-tetramethylthiouram disulfide, disclosed by U.S. Pat. No. 5,166,387). The wash may be a suitable solvent, such as acetonitrile.

The oxidation step is followed by a capping step, which although not illustrated herein, is an important step for synthesis, as it causes free 5'-OH groups, which did not undergo coupling in step 1, to be blocked from being coupled in subsequent synthetic cycles. Suitable capping reagents are set forth in Caruthers et al., Köster et al., and other patents described herein. Suitable capping reagents include a combination of acetic anhydride and N-methylimidazole.

Synthetic cycle steps (1)-(4) are repeated (if so desired) n-1 times to produce a support-bound oligonucleotide:

Support-Bound Oligonucleotide

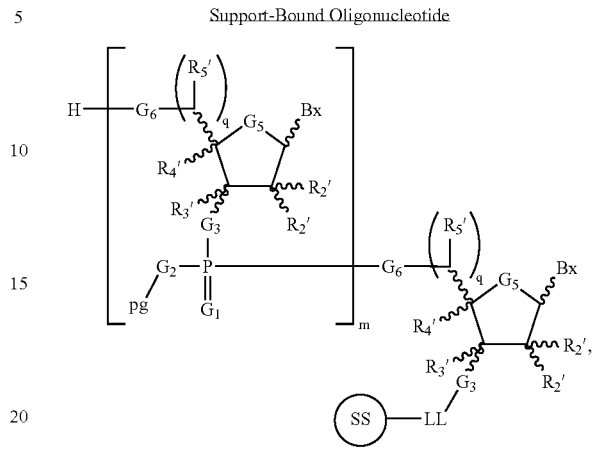

wherein each of the variables is as herein defined.

In general, the protecting group pg may be removed by a method as described by Caruthers et al. or Köster et al., supra. Where pg is a cyanoethyl group, the methodology of Köster et al., e.g. reaction with a basic solution, is generally suitable for removal of the phosphorus protecting group. In some cases it is desirable to avoid formation of adducts such as the N1-cyanoethyl thymidine group. In these cases, it is desirable to include in the reagent a tertiary amine, such as triethylamine (TEA) as taught in U.S. Pat. No. 6,465,628, which is expressly incorporated herein by reference. In general, where the nucleobases are protected, they are deprotected under basic conditions. The deprotected oligonucleotide is cleaved from the support to give the following 5'-protected oligonucleotide:

Free 5'-Protected Oligonucleotide

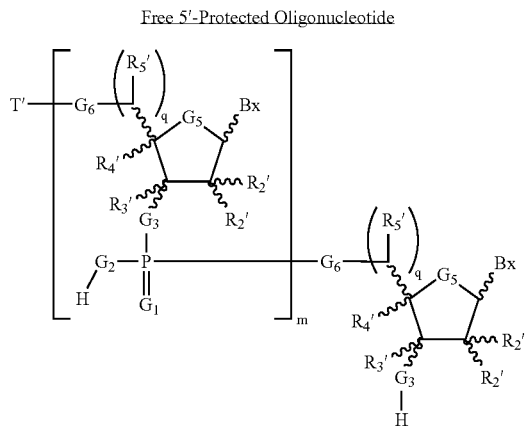

which may then be purified by reverse phase liquid chromatography, deprotected at the 5'-end in acetic acid, desalted, lyophilized or otherwise dried, and stored in an inert atmosphere until needed. Optionally, the $G_3H$ group may be derivatized with a conjugate group. The resulting oligonucleotide may be visualized as having the formula:

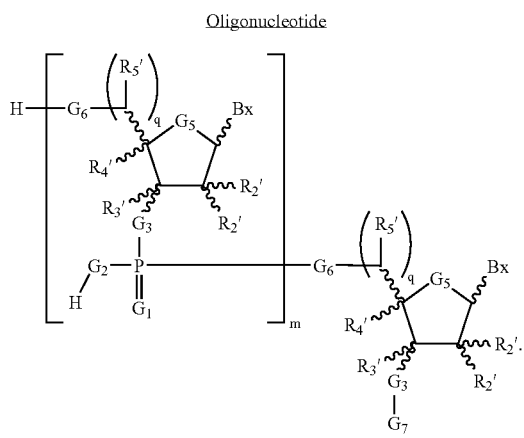

While synthesis on a solid phase support medium is known, there is a need for a solid support medium that has improved properties, especially with respect to loading (expressed in mmol of first nucleoside bound to the solid support medium per gram of solid support medium, or simply mmol/g), consistent swelling properties during the various synthesis cycles, and quality of full length oligomer produced during synthesis. Additionally, the support should be facile to manufacture. This invention is directed to these, as well as other, important ends.

SUMMARY OF THE INVENTION

In some embodiments, the present invention provides processes for making polymeric beads comprising providing an organic phase and contacting said organic phase with an aqueous phase, under conditions of time, temperature and pressure effective to form the polymeric bead.

In some embodiments, the organic phase comprises monomers, an initiator and organic solvent(s), and the aqueous phase comprises water and a dispersing reagent. In preferred embodiments the monomers comprise olefin monomers, a cross-linking monomer and a functionalizing monomer. In other preferred embodiments, the organic solvent(s) comprises one or more liquid hydrocarbons; and/or an alcohol having from five to twelve carbon atoms. In another preferred embodiment of the invention the olefin monomers comprise one or more aryl-vinyl compound and preferably comprise styrene and/or ethylstyrene. In another preferred embodiment the cross-linking monomer is an olefinic cross-linking monomer having two unconjugated vinyl groups, preferably attached to an aromatic moiety, wherein the aromatic moiety is a 5 or six member aromatic ring, and most preferably is divinylbenzene In another preferred embodiment the functionalizing monomer is an olefinic monomer having a protected functional group, which, when deprotected, yields a functional group capable of reacting with an acid or an acid anhydride to form an ester or an amide, or an olefinic monomer, having a protected hydroxyl group, and is preferably acetoxystyrene. In another preferred embodiment, the initiator is a stabilized peroxide or azo compound, most preferably being benzoylperoxide. In another preferred embodiment, the organic solvent comprises one or more liquid alkanes, benzene, toluene, xylenes and/or an alcohol having from five to twelve carbon atoms, where preferably the organic solvent comprises one or more octanes, and most preferably isooctane, and/or 2-ethylhexanol. In another preferred embodiment, the dispersing reagent comprises a polyalcohol, preferably polyvinyalcohol In some embodiments of the invention, the various components are present in the following quantities: the percentage by weight of olefin monomers initially present in monomers is from about 60% to about 96%; the percentage by weight of cross-linking monomer initially present in the monomers is from about 3% to 9.9%; the percentage by weight of the functionalizing monomer initially present in the monomers is from about 1% to about 20%; the percentage by weight of monomers initially present in the organic phase is from about 33% to about 67%; the percentage by weight of the organic solvent initially present in the organic phase is from about 33% to about 67%; the percentage by weight of liquid hydrocarbon present in the organic solvent is from about 0% to about 80%; the percentage by weight of an alcohol having from five to twelve carbon atoms initially present in the organic solvent is from about 20% to about 100%, and the percentage by weight of the dispersing reagent initially present in the aqueous phase is from about 0.01% to about 20%.

In other preferred embodiments, the various components are present in the following quantities: the percentage by weight of olefin monomer initially present in monomers is from about 75% to about 94%; the percentage by weight of cross-linking monomer initially present in the monomers is from about 4% to 9.9%; the percentage by weight of the flnctionalizing monomer initially present in the monomers is from about 2% to about 10%; the percentage by weight of monomers initially present in the organic phase is from about 35% to about 60%; the percentage by weight of the organic solvent initially present in the organic phase is from about 40% to about 65%; the percentage by weight of hydrocarbon present in the organic solvent is from about 5% to about 70%, and the percentage by weight of an alcohol having from five to twelve carbon atoms initially present in the organic solvent is from about 30% to about 95%.

In yet other preferred embodiments, the various components are present in the following quantities: the percentage by weight of olefin monomer initially present in monomers is from about 82% to about 91.5%; the percentage by weight of cross-linking monomer initially present in the monomers is from about 5.5% to 9.9%; the percentage by weight of the functionalizing monomer initially present in the monomers is from about 3% to about 8%; the percentage by weight of monomers initially present in the organic phase is from about 40% to about 50%; the percentage by weight of the organic solvent initially present in the organic phase is from about 50% to about 60%; the percentage by weight of liquid hydrocarbon present in the organic solvent is from about 10% to about 60%, and the percentage by weight of an alcohol having from five to twelve carbon atoms initially present in the organic solvent is from about 40% to about 90%.

In certain other embodiments of the invention the contacting of said organic phase with said aqueous phase takes place at a temperature of about 25° C. to about 95° C., more preferably at about 70° C. to about 85° C., and most preferably at about 75° C. to about 80° C.

The invention also provides methods for synthesizing a polynucleotide of a predetermined sequence, which comprises using a polystyrene support made from a plurality of monomers comprising a cross-linking monomer wherein the cross-linking monomer initially present in said plurality of monomers is from about 3% to 9.9% by weight. In some preferred embodiments the cross-linking monomer initially present in said plurality of monomers is from about 5.5% to 9.9%, and is most preferably about 7%. In other preferred embodiments the cross-linking monomer is divinylbenzene.

The invention further provides polymeric beads formed by any of the processes described herein. In some embodiments the beads have a loading capability of from about 100 µmole per gram of bead to about 350 µmole per gram of bead. In some embodiments the beads have an average particle size of from about 5 to about 500 µm, preferably from about 10 to about 300 µm and most preferably from about 30 to about 150 µm. In some embodiments the beads have an average pore size of from about 5 to about 500 nm, preferably from about 10 to about 100 nm and most preferably from about 20 to about 100 nm. In some embodiments the beads have a specific surface area of from about 5 to about 200 m²/g, preferably from about 10 to about 100 m²/g and most preferably from about 20 to about 70 m²/g.

The invention also provides compounds of Formula I or Formula II:

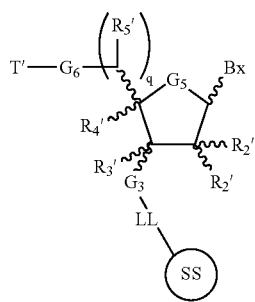

I wherein:
G$_3$ is O, S, CH$_2$, or NH;
G$_5$ is O, S, CH$_2$, CFH, CF$_2$, or —CH═CH—;
G$_6$ is O, S, CH$_2$, or NH;
each R$_2$' is H, OH, O-rg, wherein rg is a removable protecting group, a 2'-substituent, or together with R$_4$' forms a bridge;
each R$_3$' is H, a substituent, or together with R$_4$' forms a bridge;
each R$_4$' is H, a substituent, together with R$_2$' forms a bridge, together with R$_3$' forms a bridge, or together with R$_5$' forms a bridge;
q is 0 or 1;
R$_5$' is H, a substituent, or together with R$_4$' forms a bridge;
Bx is a nucleobase;
T' is H or a removable protecting group;
LL is a linking moiety; and
SS is a bead produced by the methods described herein.

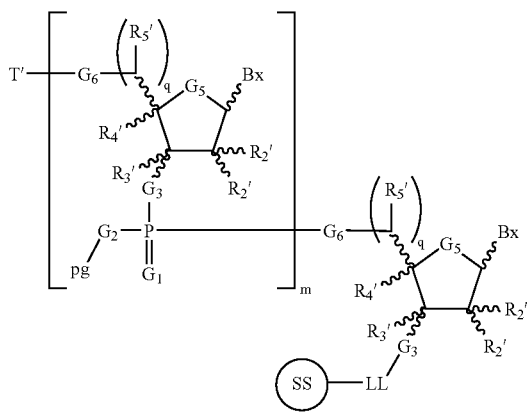

II wherein:
m is an integer from 0 to about 100;
each G$_1$ is O or S;
each G$_2$ is OH or SH;
each G$_3$ is O, S, CH$_2$, or NH;
each G$_5$ is O, S, CH$_2$, CFH, CF$_2$, or —CH═CH—;
each R$_2$' is H, OH, O-rg, wherein rg is a removable protecting group, a 2'-substituent, or together with R$_4$' forms a bridge;
each R$_3$' is H, a substituent, or together with R$_4$' forms a bridge;
each R$_4$' is H, a substituent, together with R$_2$' forms a bridge, together with R$_3$' forms a bridge, or together with R$_5$' forms a bridge;
each q is 0 or 1;
each R$_5$' is H, a substituent, or together with R$_4$' forms a bridge;
each G$_6$ is independently O, S, CH$_2$ or NH;
each Bx is a nucleobase;
pg is a removable phosphorous protecting group;
T' is a removable protecting group;
LL is a linking moiety; and
SS is a bead produced by the methods described herein.

In other embodiments, the present invention provides processes of making polymeric beads comprising (a) providing an organic phase comprising an olefin monomer, a cross-linking monomer, a functionalizing monomer and an initiator; and (b) contacting the organic phase with an aqueous phase under conditions of time, temperature effective to form the polymeric bead.

In some embodiments, the aqueous phase comprises water and a dispersing reagent, which, in some embodiments, comprises a polyalcohol, for example polyvinyl alcohol.

In some embodiments, the aqueous phase comprises water and a dispersing reagent, which, in some embodiments, comprises a polyalcohol; and the organic phase further comprises an organic solvent, the organic solvent comprising one or more liquid hydrocarbon and/or an alcohol having from 5 to 12 carbon atoms.

In some embodiments, the olefin monomer contains a single non-aromatic unsaturated group. In some further embodiments, the olefin monomer is an aryl-vinyl compound, for example styrene.

In some embodiments, the cross-linking monomer is an olefinic cross-linking monomer. In some embodiments, the cross-linking monomer is an olefinic cross-linking monomer having two unconjugated vinyl groups. In some further embodiments, the cross-linking monomer is an olefinic cross-linking monomer having two unconjugated vinyl groups attached to an aromatic moiety; wherein the aromatic moiety is a 5 or six member aromatic ring. In some embodiments, the cross-linking monomer is divinylbenzene.

In some embodiments, the functionalizing monomer is an olefinic functionalizing monomer having a protected functional group, which, when deprotected, yields a functional group suitable for reaction with an acid or an acid anhydride, preferably to form an ester or an amide. In some embodiments, the functionalizing monomer is an olefinic monomer having a protected hydroxyl group. In some embodiments, the functionalizing monomer is one or more of propanoyloxystyrene or acetoxystyrene, with acetoxystyrene being most especially preferred.

In some embodiments, the organic phase further comprises an organic solvent, which, in some embodiments, comprises one or more liquid hydrocarbons and/or an alcohol having from 5 to 12 carbon atoms. In some embodiments, the organic solvent comprises one or more liquid hydrocarbons, for example one or more liquid alkanes, benzene, toluene, xylene, for example octanes, for example isooctane and/or an alcohol having from 5 to 12 carbon atoms, for example 2-ethylhexanol.

In some embodiments, the polymerization initiator is a stabilized peroxide, for example benzoylperoxide or azo compound.

In some embodiments, the olefin monomer is an arylvinyl compound, and the cross-linking monomer is an olefinic cross-linking monomer having two unconjugated vinyl groups. In further embodiments, the olefin monomer is an aryl-vinyl compound, and the cross-linking monomer is an olefinic cross-linking monomer having two unconjugated vinyl groups attached to an aromatic moiety; wherein the aromatic moiety is a 5 or six member aromatic ring. In some further embodiments, the olefin monomer is styrene, and the cross-linking monomer is divinylbenzene. In some further embodiments, the olefin monomer is an aryl-vinyl compound, and the functionalizing monomer is an olefinic monomer having a protected functional group, which, when deprotected, yields a functional group capable of reacting with an acid or an acid anhydride to form an ester or an amide.

In some embodiments, the olefin monomer is an arylvinyl compound, and the functionalizing monomer is an olefinic monomer having a protected hydroxyl group. In further embodiments, the olefin monomer is styrene or ethylstyrene, and the functionalizing monomer is acetoxystyrene. In still further embodiments, the cross-linking monomer is an olefinic monomer having two unconjugated vinyl groups attached to an aromatic moiety; wherein the aromatic moiety is a five or six member aromatic ring, and the functionalizing monomer is an olefinic monomer having a protected functional group, which, when deprotected, yields a functional group capable of reacting with an acid or an acid anhydride to form an ester or an amide. In still further embodiments, cross-linking monomer is an olefinic cross-linking monomer having two unconjugated vinyl groups attached to an aromatic moiety; wherein the aromatic moiety is a five or six member aromatic ring, and the functionalizing monomer is an olefinic monomer having a protected hydroxyl group. In still further embodiments, the cross-linking monomer is divinylbenzene, and the functionalizing monomer is acetoxystyrene.

In some embodiments, the olefin monomer is an arylvinyl compound, the cross-linking monomer is an olefinic cross-linking monomer having two unconjugated vinyl groups attached to an aromatic moiety; wherein the aromatic moiety is a five or six member aromatic ring, and the functionalizing monomer is an olefinic monomer having a protected functional group, which, when deprotected, yields a functional group capable of reacting with an acid or an acid anhydride to form an ester or an amide.

In further embodiments, the olefin monomer is an arylvinyl compound, the cross-linking monomer is an olefinic cross-linking monomer having two unconjugated vinyl groups attached to an aromatic moiety; wherein the aromatic moiety is a five or six member aromatic ring, and the functionalizing monomer is an olefinic monomer having a protected hydroxyl group.

In further embodiments, the olefin monomer is styrene, the cross-linking monomer is divinylbenzene, and the functionalizing monomer is acetoxystyrene.

In some of each of the foregoing embodiments, the aqueous phase comprises water and a dispersing reagent, which, in some embodiments, comprises polyvinylalcohol.

In some embodiments, of the foregoing processes, said contacting further comprises agitating the aqueous and organic phases, for example by stirring the aqueous and organic phases. In further embodiments, the processes of the invention further comprise the step of washing the bead. In some embodiments, the bead is washed with one or more wash solvents, at least one of the wash solvent comprising acetone, water or methanol.

In some embodiments of the foregoing processes, the divinylbenzene is initially present in the organic phase in an amount that is about 3 to about 20 percent by weight of the total monomers initially present in the organic phase; or about 4 to about 15 percent by weight of the total monomers initially present in the organic phase; or about 5.5 to about 10 percent by weight of the total monomers initially present in the organic phase.

In some embodiments of the foregoing processes, the acetoxystyrene is initially present in the organic phase in an amount that is about 1 to about 20 percent by weight of the total monomers initially present in the organic phase; or about 2 to about 10 percent by weight of the total monomers initially present in the organic phase; or about 3 to about 8 percent by weight of the total monomers initially present in the organic phase.

In some embodiments wherein the aqueous phase comprises water and a dispersing reagent, the organic phase further comprises an organic solvent, the organic solvent comprising one or more liquid hydrocarbon and/or an alcohol having from 5 to 12 carbon atoms. In some such embodiments, the percentage by weight of organic solvent initially present in the organic phase is from about 33% to about 67%; the percentage by weight of the total monomer initially present in the organic phase is from about 33% to about 67%; the percentage by weight of olefin monomer initially present in the total monomers is from about 60% to about 96%; the percentage by weight of cross-linking monomer initially present in the monomers is from about 3% to about 20%; the percentage by weight of the functionalizing monomer initially present in the monomers is from about 1% to about 20%, and the percentage by weight of hydrocarbon present in the organic solvent is from about 0% to about 80%; and the percentage by weight of an alcohol having from 5 to 12 carbon atoms initially present in the organic solvent is from about 20% to about 100%. In further such embodiments, the percentage by weight of organic solvent initially present in the organic phase is from about 40% to about 65%; the percentage by weight of the total monomers initially present in the organic phase is from about 35% to about 60%; the percentage by weight of olefin monomer initially present in the monomers is from about 75% to about 94%; the percentage by weight of cross-linking monomer initially present in the total monomers is from about 4% to about 15%; the percentage by weight of functionalizing monomer initially present in the total monomers is from about 3% to about 8%, and the percentage by weight of hydrocarbon present in the organic solvent is from about 5% to about 70%; and the percentage by weight of an alcohol having from 5 to 12 carbon atoms initially present in the organic solvent is from about 30% to about 95%. In still further such embodiments, the percentage by weight of organic solvent initially present in the organic phase is from about 50% to about 60%; the percentage by weight of the total monomers initially present in the organic phase is from about 40% to about 50%; the percentage by weight of olefin monomer initially present in total monomers is from about 82% to about 91.5%; the percentage by weight of cross-linking monomer initially present in total monomers is from about 5.5% to about 10%; the percentage by weight of the functionalizing monomer initially present in the monomers is from about 3% to about 8%, and the percentage by weight of hydrocarbon present in the organic solvent is from about 10% to about 60%; and the percentage by weight of an alcohol having from 5 to 12 carbon atoms initially present in the organic solvent is from about 40% to about 90%. In some such embodiments, the dispersing reagent comprises polyvinylalcohol. In further such embodiments, the olefin monomer is styrene or ethylstyrene, the cross-linking monomer is divinylbenzene, the functionalizing monomer is acetoxystyrene, the hydrocarbon is isooctane, and an alcohol having from 5 to 12 carbon atoms is 2-ethylhexanol. In some such embodiments, the percentage by weight of the dispersing reagent initially present in the aqueous phase is from about 0.01% to about 20%.

In some embodiments of the processes described herein, the organic phase and aqueous phase are heated to a temperature of about 25° C. to about 95° C.; or about 40° C. to about 90° C.; or about 70° C. to about 85° C.; or about 75° C. to about 80° C.

The present invention further provides processes of making a support-bound nucleoside, comprising (a) providing a polymeric bead produced by the process of the invention, and optionally reacting said bead with an activating reagent to provide an activated polymeric bead; (b) reacting said optionally activated polymeric bead with at least one linking reagent to produce a bead having a support-bound linker; and (c) linking said support-bound linker with a nucleoside to form a support-bound nucleoside.

The present invention further provides processes of making a support-bound nucleoside, comprising (a) providing a polymeric bead produced by the process of the invention, and optionally reacting said bead with an activating reagent to provide an activated polymeric bead; and (b) reacting said optionally activated polymeric bead with a linker-bearing nucleoside to prepare the support-bound nucleoside.

The present invention further provides processes of making an oligonucleotide, comprising: (a) providing a support-bound nucleoside made by any of the foregoing processes of the invention as described herein, said support-bound nucleoside having at least one protected hydroxyl group; (b) deprotecting a hydroxy group of the support-bound nucleoside; (c) contacting the support-bound nucleoside with an activated protected nucleoside to produce a phosphite intermediate; (d) contacting the phosphite intermediate with an oxidizing reagent to produce a phosphotriester intermediate; (e) optionally capping unreacted nucleosides; (f) optionally repeating steps (b)-(e) at least one time; and (g) cleaving the oligonucleotide from the solid support. In some such embodiments, the deprotecting step of step (b) comprises the removal of an acid-labile protecting group.

The present invention further provides processes of making an oligonucleotide, comprising: (a) providing a support-bound nucleoside made by any of the foregoing processes of the invention as described herein, said support-bound nucleoside having at least one protected hydroxyl group; (b) deprotecting a hydroxy group of the support-bound nucleoside; (c) contacting the support-bound nucleoside with an activated protected nucleoside to produce a phosphite intermediate; (d) contacting the phosphite intermediate with an oxidizing reagent to produce a phosphotriester intermediate; (e) optionally capping unreacted nucleosides; (f) optionally repeating steps (b)-(e) at least one time; and (g) cleaving the oligonucleotide from the solid support. In some such embodiments, the deprotecting step of step (b) comprises the removal of an acid-labile protecting group.

The present invention further provides compounds of Formula I:

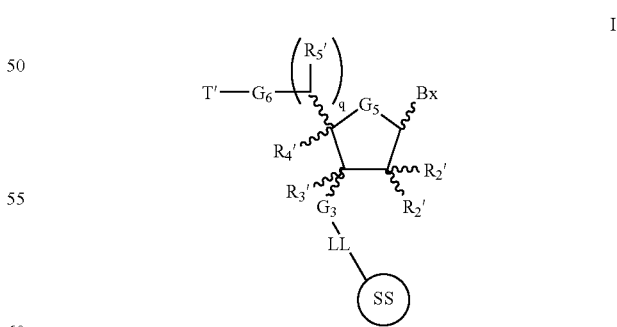

wherein LL is a linking moiety; SS is a bead of the invention as described herein; and the other constituent variables are as described infra. In some embodiments, $G_3$, $G_5$ and $G_6$ are each O; an in further embodiments, one $R_2'$ is H, and $R_3'$ and $R_4'$ are each H.

The present invention further provides compounds of Formula II:

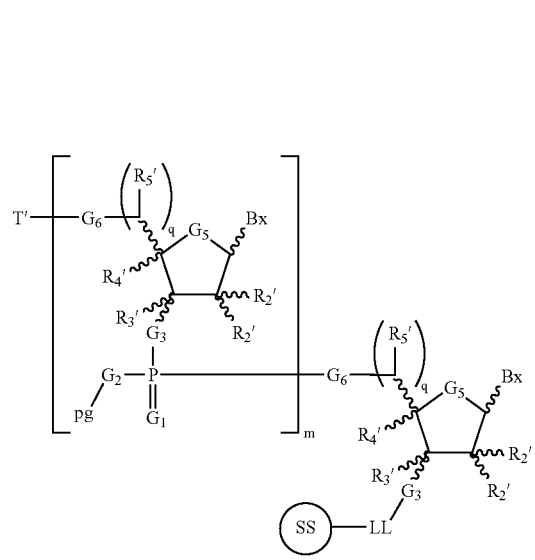

II

Wherein the constituent variables are as described infra. In some embodiments, each $G_3$, $G_5$ and $G_6$ is O. In further such embodiments, one each pair of vicinal $R_2'$ groups is H, and each $R_3'$ and each $R_4'$ is H.

The present invention further provides processes for the preparation of compound of Formula I above, the method comprising: a) providing a compound of Formula III:

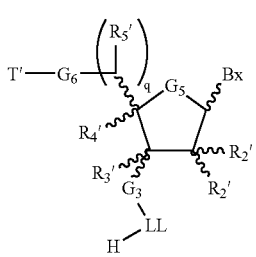

III and b) reacting the compound of Formula III with the bead of the invention as described herein, under conditions effective for form the compound of Formula I. In some embodiments, $G_3$, $G_5$ and $G_6$ are each O. In further embodiments, one $R_2'$ is H, and $R_3'$ and $R_4'$ are each H.

The present invention also provides processes for the preparation of a compound of Formula I, the method comprising: a) providing a bead of the invention as described herein; b) attaching one end of a bifunctional linker LL to a functional group of the bead; and c) reacting the other end of the bifunctional linker LL with a compound of Formula IV:

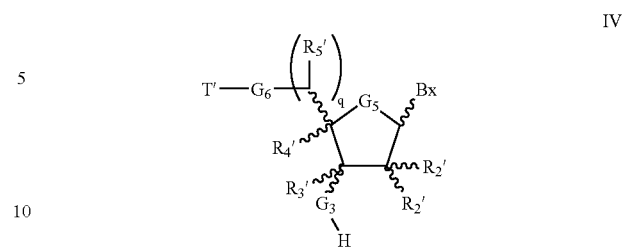

IV to form the compound of Formula I. In some embodiments, $G_3$, $G_5$ and $G_6$ are each O. In further embodiments, one $R_2'$ is H, and $R_3'$ and $R_4'$ are each H.

The present invention further provides processes for the preparation of a compound of Formula II:

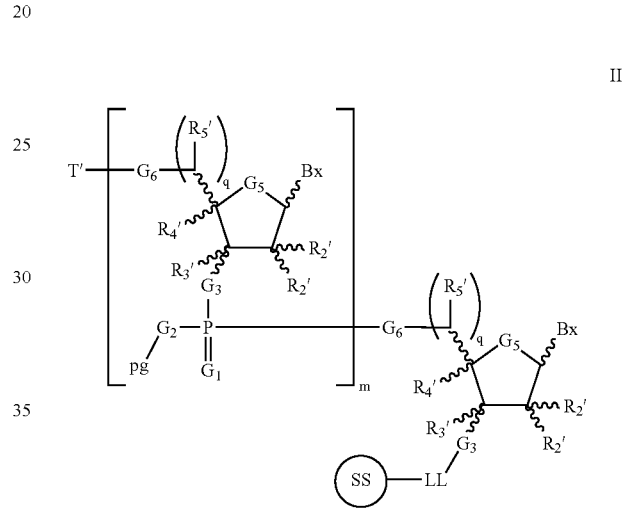

II

Wherein LL is a linking moiety, SS is a bead of the invention as described herein, and the other constituent variables are as described infra, the method comprising: a) providing a compound of Formula I as described above:

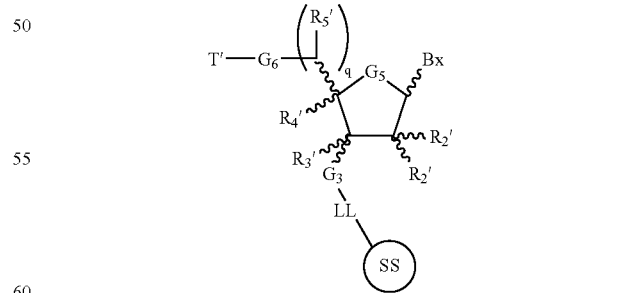

I wherein T' is a removable protecting group; b) removing the protecting group T' to form a deprotected support bound nucleoside; c) reacting the deprotected support bound nucleoside of step (b) with a protected nucleoside amidite or Formula V:

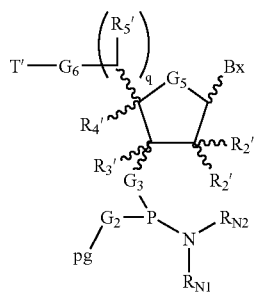

wherein the constituent variables are as defined infra; to form a phosphite compound of Formula VI:

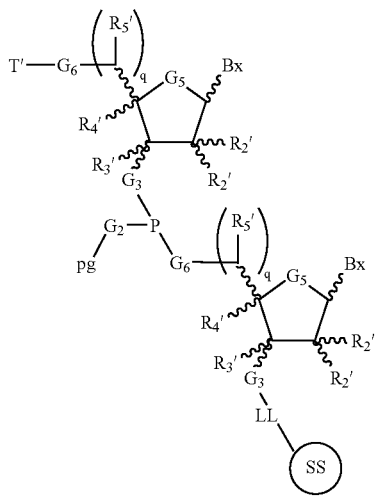

d) oxidizing or sulfurizing the phosphate of Formula VI to form a compound of Formula II, wherein m is 1; e) optionally capping unreacted nucleosides; and f) optionally repeating steps (b)-(e) one or more times. In some embodiments, each $G_3$, $G_5$ and $G_6$ is O. In further embodiments, one each pair of vicinal $R_2'$ groups is H, and each $R_3'$ and each $R_4'$ is H.

In some embodiments of the foregoing synthetic processes, the process further comprises cleaving the resulting oligonucleotide from the solid support.

The present invention further provides processes for preparing an oligomer comprising amino acid monomers, the method comprising: (a) providing a polymer substrate, said polymer substrate having the formula SS-LL-ZZ, wherein SS is a polymeric bead of the invention, LL is an optional linker, and ZZ is a chemical group capable of forming an anchoring linkage with either the carboxyl group or the amino group of an amino acid; (b) coupling a first amino acid synthon, having a protecting group at either the carboxyl group or the amino group thereof, with the polymer substrate; (c) removing the protecting group from the coupled first amino acid to generate a free amino or carboxyl group; and (d) reacting the free amino or carboxyl group with a second amino acid synthon, to form a peptide chain. In some embodiments, the processes further comprise the steps of: (e) removing the protecting group from the second amino acid synthon to generate a terminal free amino or carboxyl group on said peptide chain; and (f) reacting said free amino or carboxyl group on said peptide chain with a further protected amino acid synthon to lengthen said peptide chain. In further embodiments, steps e and f are performed a plurality of times. Some embodiments further comprise cleaving said anchoring linkage without substantially degrading said peptide chain. In some embodiments, the amino acid synthons are naturally occurring amino acids. In other embodiments, the amino acid synthons are peptide nucleic acid synthons.

The present invention further provides processes for preparing a compound of Formula X:

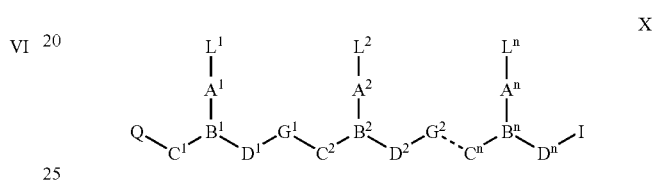

wherein the constituent variables are as defined infra, the process comprising the steps of: (a) providing a polymer substrate, said polymer substrate has the formula SS-LL-ZZ, wherein SS is a polymeric bead of claim 67, LL is a linker, and ZZ is a chemical group capable of forming an anchoring linkage with an amino acid; (b) coupling said polymer substrate with a first amino acid through said anchoring linkage, said first amino acid having formula (XX):

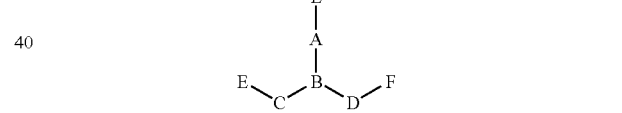

wherein the constituent variables are as defined infra, (c) removing said amino protecting group from said coupled first amino acid to generate a free amino group; and (d) reacting said free amino group with a second amino acid having formula (XX) to form a peptide chain. In some embodiments, the processes further comprising the steps of: (e) removing said amino protecting group from said second amino acid to generate a terminal free amino group on said peptide chain; and (f) reacting said free amino group on said peptide chain with a further amino acid having formula (XX) to lengthen said peptide chain. In some embodiments, steps e and f are performed a plurality of times. Some embodiments further comprise removing at least one protecting group remaining on the amino acid moieties of the peptide chain. Some embodiments further comprise cleaving the anchoring linkage without substantially degrading said peptide chain. In some embodiments, the chemical group capable of forming said anchoring linkage is chloro-, bromo- and iodo-substituted alkyl, amino-substituted alkyl, amino and aryl-substituted alkyl, amino- and alkylaryl-substituted alkyl, hydroxy-substituted alkyl, or a derivative thereof having a spacer group that can be cleaved substantially without degradation of said polypeptide. In some embodiments, chloro-substituted alkyl is chloromethyl, amino-substituted alkyl is aminomethyl, amino- and alkyl-substituted aryl is "-aminobenzyl, amino- and alkylaryl-substituted alkyl is selected from the group consisting of "-amino-3- and "-amino-4-methylbenzyl, and hydroxy-substituted alkyl is hydroxymethyl. In some embodiments, the chemical group is derived from an amino-containing moiety selected from amino-substituted alkyl, amino- and aryl substituted alkyl, and amino- and alkylaryl-substituted alkyl; and the chemical group includes a spacer group derived from the group consisting of 4-(haloalkyl)aryl-lower alkanoic acids, Boc-aminoacyl-4-(oxymethyl)aryl-lower alkanoic acids, N-Boc-p-acylbenzhydrylamines, N-Boc-4'-(lower alkyl)-p-acylbenzhydrylamines, N-Boc-4'-(lower alkoxy)-p-acylbenzhydrylamines, and 4-hydroxymethylphenoxy-lower alkanoic acids.

In some embodiments, the compound X has the formula:

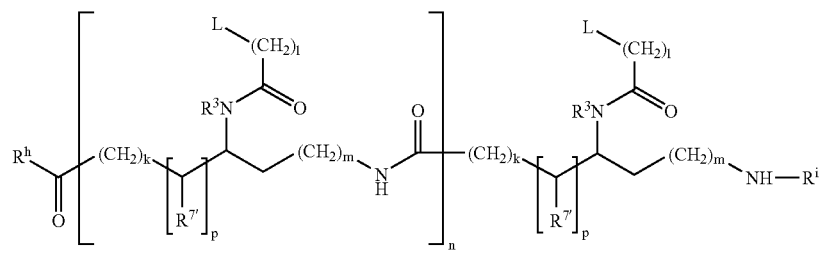

wherein the constituent variables are as defined infra.

In further embodiments, the compound X has the formula:

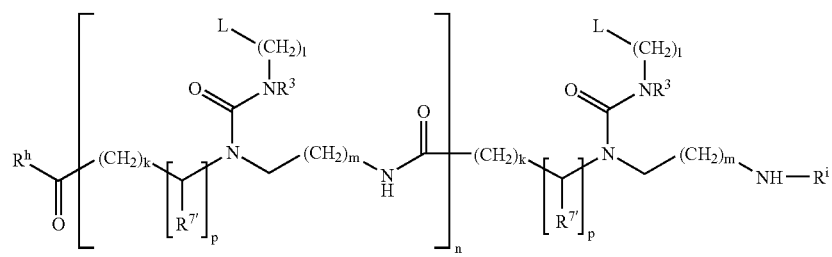

Wherein the constituent variables are as defined infra.

In some embodiments, the amino acid having formula (XX) has the formula:

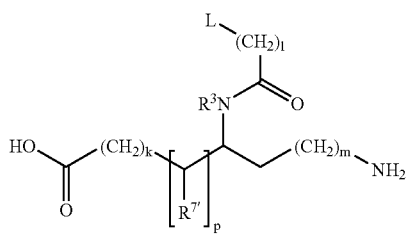

wherein the constituent variables are as defined infra.

In further embodiments, the amino acid having formula (XX) has the formula:

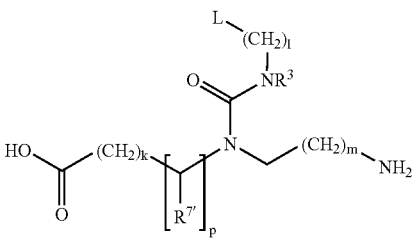

wherein the constituent variables are as defined infra.

In some embodiments, the polymeric beads of the invention have a loading capability of at least about 50 μmole per gram of bead; of at least about 100 μmole per gram of bead; of at least about 150 μmole per gram of bead; of at least about 200 μmole per gram of bead; of at least about 250 μmole per gram of bead; of at least about 300 μmole per gram of bead; of at least about 350 μmole per gram of bead; of at least about 400 μmole per gram of bead; or at least about 450 μmole per gram of bead. In some embodiments, the bead has a loading capability of from about 100 μmole per gram of bead to about 350 μmole per gram of bead.

Advantageously, beads of the present invention are relatively easy to manufacture and to use with a variety of linkers and nucleosides. Additionally, beads of the present invention can be used in a variety of automated solid-phase synthesis instruments. The beads of the present invention have superior loading capacity, being capable of containing greater than 100 mmol of first nucleoside/oligonucleotide per gram of support. The beads of the present invention also have excellent physical properties, including compatibility with a variety of synthetic reagents and solvents, consistent swelling properties across a spectrum of synthetic solutions, a favorable backpressure profile, excellent uniformity in bead and pore size, and resultant good synthetic (full length oligomer) performance.

The processes of making the beads of the present invention are easily implemented, are scalable and have excellent cost profiles. In addition the advantages in regard to the relative ease of manufacture and use described above, the beads of the present invention are amenable to the use of a variety of linkers that may be employed for covalently attaching nucleoside, amino acids, or derivatives of either, to the support. Additionally, the beads of the present invention permit efficient manufacture of high-quality (full length) oligonucleotide and other polymeric species.

DETAILED DESCRIPTION OF THE INVENTION

The present invention provides cross-linked, functionalized polymeric beads for oligomer synthesis, methods of making the same, methods of using the same in oligomer synthesis, support-bound nucleosides, and methods of making and using the same, as well as support-bound oligonucleotides and amide-linked oligomers, methods of using the same, and oligonucleotides and amide linked oligomers made using polymeric beads according to the present invention.

In some embodiments, the beads are made by a process comprising: (a) providing an organic phase comprising an olefin monomer, a cross-linking monomer, a functionalizing monomer and an initiator; and (b) contacting the organic phase with an aqueous phase under conditions of time, temperature effective to form the polymeric bead.

In some embodiments, the beads of the invention comprise crosslinked polyolefin. In some preferred embodiments, the inventive beads comprise cross-linked polystyrene. In accordance with the methods of the invention described herein, the beads are formed by the free-radical reaction of a composition comprising an olefin and crosslinker under conditions suitable to form a bead having the desired properties. A preferred olefin is styrene.

The aqueous phase generally includes water and a dispersing reagent, which is believed to promote the formation of stable beads. The dispersing reagent can be a single compound, or a mixture of dispersing agents. In some embodiments, the dispersing reagent includes one or more polyalcohols, polyacrylic acid, carboxymethyl cellulose, gelatin, calcium carbide, calcium phosphate, calcium sulfate, barium sulfate, bentonite. In some preferred embodiments, the dispersing reagent either includes or consists of polyvinyl alcohol. In some embodiments, the dispersing reagent is present in the aqueous phase at an amount that is from about 0.01% to about 20%, or from about 0.1% to about 10%, of the weight of the aqueous phase.

The organic phase includes an olefin monomer, a cross-linking monomer, a functionalizing monomer, and an initiator. In some embodiments, the organic phase further comprises one or more organic solvents.

In some embodiments, the olefin monomer contains a single non-aromatic unsaturated group, for example a vinyl group. Preferably, the olefinic monomer also contains an aryl moiety, for example a phenyl group. Thus, in some preferred embodiments, the olefin monomer is an aryl-vinyl compound. In a particularly preferred embodiment, the olefin monomer is styrene or ethylstyrene.

The organic phase includes one or more cross-linking monomer, i.e., difunctional compounds that cross-link polymerized chains. In some embodiments, the cross-linking monomer is a bis-olefinic cross-linking monomer; i.e., a molecule containing at least two carbon-carbon double bonds capable of forming separate linkages. In some embodiments, the olefinic cross-linking monomer has two unconjugated vinyl groups. In some embodiments, the olefinic cross-linking monomer has two unconjugated vinyl groups attached to an aromatic moiety, which, in some embodiments, is a five or six member aromatic ring, for example a phenyl ring. In one preferred embodiment, cross-linking monomer is 1,2-, 1,3-, or 1,4-divinylbenzene, or a mixture of one or more thereof. More preferably, the cross-linking monomer includes or is composed of 1,3- or 1,4-divinylbenzene.

The beads of the invention further comprise one or more types of functional groups, which are contributed by one or more functionalizing monomer. A functionalizing monomer is a polymer or preferably a monomer that contributes a functional group capable of forming a covalent linkage to a linker moiety or directly to a nucleoside, an amino acid, or a functional group of a core moiety for combinatorial synthesis. In especially preferred embodiments the functional group is —OH. The functional group may be contributed by a functionalizing monomer that is reactive with styrene and/or the cross-linking monomer during polymerization. In some embodiments, the functionalizing monomer possesses at least one olefinic group covalently attached to a functional group. In some preferred embodiments, the functionalizing group is acyloxyl group.

In particularly preferred embodiments, the functionalizing agent has the formula:

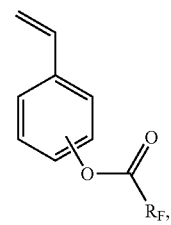

wherein $R_F$ is selected from substituted or unsubstituted $C_1$-$C_{10}$ alkyl.

Especially preferred functionalizing monomers are acetoxystyrene, propanoyloxystyrene, with acetoxystyrene being most especially preferred.

In some embodiments, the functional groups are protected with one or more protecting groups, which must be removed prior to oligomer synthesis. Such functional groups include acyl groups, e.g. acetyl, propanoyl, benzoyl and other functional group protecting groups. Accordingly, embodiments of the invention include both protected and deprotected functionalized, cross-linked polyolefinic polymers. In some embodiments, the functional group, when deprotected, yields a functional group suitable for reaction with acid or an acid anhydride, preferably to form an ester or an amide.

The organic phase can further include one or more organic solvents. Suitable solvents include one or more liquid hydrocarbons and/or alcohol having from five to 12 carbon atoms. In some embodiments, the organic solvent includes one or more liquid hydrocarbons, preferably one or more liquid alkanes, benzene, toluene, xylenes, for example one or more octanes and/or an alcohol having from five to twelve carbon atoms. In preferred embodiment, the organic solvent includes isooctane and 2-ethylhexanol.

The organic phase can further include one or more initiators. Suitable initiators include compounds that are capable of initiating free radical polymerization reactions, for example stabilized peroxides or azo compounds. In some preferred embodiments, the initiator is selected from benzoyl peroxide, dilauroyl peroxide, 1,1-di(t-butylperoxy)-2-methylcyclohexane, di-t-butyl peroxide, distearoyl peroxide, di-t-hexyl peroxide, t-butyl cumyl peroxide, 1,1-di(t-hexyl peroxy)-3,3,5-trimethylcyclohexane, 1,1-di(t-butylperoxy)cyclohexane, 1,1,3,3-tetramethylbutylperoxy-2-ethylhexanoate, t-hexyl peroxy-2-ethylhexanoate, 2,2'-azobisisobutyronitrile, 2,2'-azobis-2-methylbutyronitrile, or 2,2'-azobis-2,4-dimethylvaleronitrile, In one preferred embodiment, the initiator includes, or comprises, benzoylperoxide.

In some preferred embodiments, the olefin monomer is styrene or ethylstyrene, the cross-linking monomer is divinylbenzene, and the functionalizing monomer is acetoxystyrene. In some such embodiments, the organic solvent is isooctane and 2-ethylhexanol, the initiator is benzoylperoxide.

In one preferred embodiment according to the present invention there is provided a process of making a functionalized, cross-linked polystyrene bead suitable for oligonucleotide synthesis, said process comprising: (a) mixing water and polyvinyl alcohol (PVA) to form an aqueous solution; (b) mixing isooctane and 2-ethylhexanol solvents, styrene monomer, divinylbenzene cross-linking monomer, benzoylperoxide initiator and acetoxystyrene functionalizing monomer to form an organic solution; and (c) mixing the aqueous solution and the organic solution to form the functionalized, cross-linked polystyrene bead suitable for oligonucleotide synthesis.

In accordance with some embodiments of the methods of the invention, the contacting of the organic and aqueous phases includes agitating the two phases, for example by stirring. In some embodiments, the two phases are agitated for up to 5, up to 7, up to 10, up to 12, or up to 15 hours or longer. In general, it is beneficial to stir the mixture of the organic and aqueous phases at a fixed speed, to promote production of the desired bead size distribution. In some preferred embodiments, the mixture is stirred by paddles, anchor paddles, propeller s or disk turbines at 250 rpm for the desired time.

Generally, the organic phase and aqueous phase are heated during agitation, to a temperature of about 25° C. to about 95° C.; about 40° C. to about 90° C.; about 70° C. 85° C.; or about 75° C. to about 80° C.

After reaction of the organic and aqueous phases, the beads are preferably washed with one or more wash solvents. In some embodiments, at least one of the wash solvents is acetone, water or methanol. Washing can be accomplished by any of the several techniques for washing solid support media, for example by filtering the reaction mixture and washing wash solvent through the beads on the filter. In some embodiments, the beads can then be separated by size to collect the beads of the desired size, for example by dispersing the beads in a suitable solvent, for example acetone, and sieving the suspension. The beads can then be dried, for example under a vacuum.

In some preferred embodiments, the cross-linking monomer, for example divinylbenzene, is initially present in the organic phase in an amount that is about 3% to about 20% by weight, about 4% to about 15% percent by weight, or about 5.5% to about 10% by weight of the total monomers initially present in the organic phase.

In further preferred embodiments, the molar ratio of the cross-linking monomer, for example divinylbenzene, to the total monomers initially present in the organic phase is from about 1:27 to about 1:8; from about 1:25 to about 1:10; or from about 1:20 to about 1:13.

In some further preferred embodiments, the functionalizing monomer, for example acetoxystyrene, is initially present in the organic phase in an amount that is about 1% to about 20% percent by weight, about 2% to about 10% percent by weight, or about 3% to about 8% by weight of the total monomers initially present in the organic phase.

In some further preferred embodiments, the molar ratio of the functionalizing monomer, for example acetoxystyrene, to the monomers initially present in the organic phase is from about 1:99 to about 1:10; or from about 1:62 to about 1:18. In some further preferred embodiments, the molar ratio is from about 1:46 to about 1:21.

In some preferred embodiments, the organic phase further comprises an organic solvent, the organic solvent comprising one or more liquid hydrocarbons and/or an alcohol having from five to twelve carbon atoms, preferably isooctane and 2-ethylhexanol; and the percentage by weight of the organic solvent initially present in the organic phase is from about 33% to about 67%, or from about 40% to about 65%, or from about 50% to about 60%;

the percentage by weight of the total monomers initially present in the organic phase is from about 33% to about 67%, or from about 35% to about 60%, or from about 40% to about 50%;

the percentage by weight of olefin monomer, preferably styrene or ethylstyrene, initially present in total monomers is from about 60% to about 96%, or from about 75% to about 94%, or from about 82% to about 91.5%;

the percentage by weight of cross-linking monomer, preferably one or more divinylbenzenes, initially present in total monomers is from about 3% to about 20%, or from about 4% to about 15%, or from about 5.5% to about 10%;

the percentage by weight of functionalizing monomer, preferably acetoxystyrene, initially present in the total monomers is from about 1% to about 20%, or from about 2% to about 10%, or from about 3% to about 8%;

the percentage by weight of hydrocarbon, preferably isooctane, present in the organic solvent is from about 0% to about 80%, or from about 5% to about 70%, or from about 10% to about 60%; and the percentage by weight of an alcohol having from five to twelve carbon atoms, preferably 2-ethytlhexanol, initially present in the organic solvent is from about 20% to about 100%, or from about 30% to about 95%, or from about 40% to about 90%.

In some such embodiments, the aqueous phase comprises water and a dispersing reagent, preferably a polyalcohol such as polyvinylalcohol, where the dispersing reagent is present in the aqueous phase at an amount that is from about 0.01% to about 20%, or from about 0.1% to about 10%, of the weight of the aqueous phase.

In some embodiments of the methods herein, the ratio of the volume of the aqueous phase to the volume of the organic phase is from about 2:3 to about 50:1; or from about 1:1 to about 20:1; or from about 3:2 to about 10:1.

The present invention also provides processes for making a support-bound nucleoside, comprising (a) providing a polymeric bead produced by a process of the invention, and optionally reacting said bead with an activating reagent to provide an activated polymeric bead; (b) reacting the activated polymeric bead with at least one linking reagent to produce a bead having a support-bound linker; and (c) linking said support-bound linker with a nucleoside to form a support-bound nucleoside.

In further embodiments, the present invention also provides processes for making a support-bound nucleoside, comprising: (a) providing a polymeric bead produced by a process of the invention, and optionally reacting said bead with an activating reagent to provide an activated polymeric bead; and (b) reacting said activated polymeric bead with a linker-bearing nucleoside to prepare the support-bound nucleoside.

In further embodiments, the present invention also provides processes for making an oligonucleotide, comprising: (a) providing a support-bound nucleoside made by a process of the invention; (b) deprotecting a hydroxy group of the support-bound nucleoside, for example by removing an acid-labile protecting group; (c) contacting the support-bound nucleoside with an activated protected nucleoside to produce a phosphite intermediate; (d) contacting the phosphite intermediate with an oxidizing reagent to produce a phosphotriester intermediate; (e) optionally capping unreacted nucleosides; (f) optionally repeating steps (b)-(e) at least one time; and (g) cleaving the oligonucleotide from the solid support.

In some embodiments, the present invention provides compounds of Formula I:

I wherein:
$G_3$ is O, S, $CH_2$, or NH;
$G_5$ is O, S, $CH_2$, CFH, $CF_2$, or —CH=CH—;
$G_6$ is O, S, $CH_2$, or NH;

each $R_2'$ is H, OH, O-rg, wherein rg is a removable protecting group, a 2'-substituent, or together with $R_4'$ forms a bridge;
each $R_3'$ is H, a substituent, or together with $R_4'$ forms a bridge;
each $R_4'$ is H, a substituent, together with $R_2'$ forms a bridge, together with $R_3'$ forms a bridge, or together with $R_5'$ forms a bridge;
q is 0 or 1;
$R_5'$ is H, a substituent, or together with $R_4'$ forms a bridge;
Bx is a nucleobase;
T' is H or a removable protecting group;
LL is a linking moiety or a single bond; and
SS is a bead of the invention as described herein.

In some preferred embodiments of the compounds of Formula I, $G_3$, $G_5$ and $G_6$ are each O. In some further preferred embodiments of the compounds of Formula I, at least one $R_2'$ is H, and $R_3'$ and $R_4'$ are each H.

Also provided in accordance with the present invention are compounds of Formula II:

II wherein:
m is an integer from 0 to about 100;
each $G_1$ is O or S;
each $G_2$ is OH or SH;
each $G_3$ is O, S, $CH_2$, or NH;
each $G_5$ is O, S, $CH_2$, CFH, $CF_2$, or —CH=CH—;
each $R_2'$ is H, OH, O-rg, wherein rg is a removable protecting group, a 2'-substituent, or together with $R_4'$ forms a bridge;
each $R_3'$ is H, a substituent, or together with $R_4'$ forms a bridge;
each $R_4'$ is H, a substituent, together with $R_2'$ forms a bridge, together with $R_3'$ forms a bridge, or together with $R_5'$ forms a bridge;
each q is 0 or 1;
each $R_5'$ is H, a substituent, or together with $R_4'$ forms a bridge;
each $G_6$ is independently O, S, $CH_2$ or NH;
each Bx is a nucleobase;
T' is a removable protecting group;
LL is a linking moiety; and
SS is a bead of the invention as described herein.

In some preferred embodiments of the compounds of Formula II, each $G_3$, $G_5$ and $G_6$ is O. In some further preferred embodiments of the compounds of Formula II, at least one of each pair of vicinal $R_2'$ groups is H, and each $R_3'$ and each $R_4'$ is H.

In further embodiments, the present invention provides processes for the preparation of a compound of Formula I:

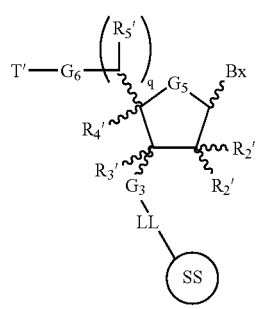

I wherein:
$G_3$ is O, S, $CH_2$, or NH;
$G_5$ is O, S, $CH_2$, CFH, $CF_2$, or —CH=CH—;
each $R_2'$ is H, OH, O-rg, wherein rg is a removable protecting group, a 2'-substituent, or together with $R_4'$ forms a bridge;
each $R_3'$ is H, a substituent, or together with $R_4'$ forms a bridge;
each $R_4'$ is H, a substituent, together with $R_2'$ forms a bridge, together with $R_3'$ forms a bridge, or together with $R_5'$ forms a bridge;
q is 0 or 1;
$R_5'$ is H, a substituent, or together with $R_4'$ forms a bridge;
Bx is a nucleobase;
pg is a removable phosphorous protecting group;
T' is a removable protecting group;
LL is a linking moiety or a single bond; and
SS is a bead of the invention as described herein; the method comprising:
a) providing a compound of Formula III:

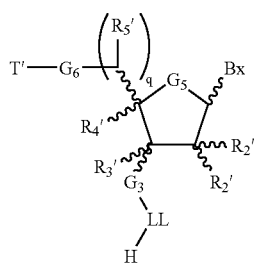

III and;
b) reacting the compound of Formula III with the bead of the invention, under conditions effective for forming the compound of Formula I. In some embodiments of the process, $G_3$, $G_5$ and $G_6$ are each O. In some further embodiments, at least one $R_2'$ is H, and $R_3'$ and $R_4'$ are each H.

In further embodiments, the present invention provides processes for the preparation of a compound of Formula I:

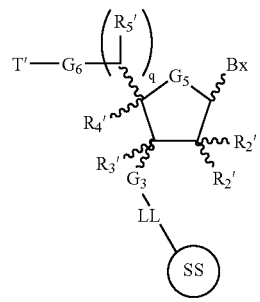

I wherein:
$G_3$ O, S, or NH;
$G_5$ is O, S, $CH_2$, CFH, $CF_2$, or —CH=CH;
each $R_2'$ is H, OH, O-rg, wherein rg is a removable protecting group, a 2'-substituent, or together with $R_4'$ forms a bridge;
each $R_3'$ is H, a substituent, or together with $R_4'$ forms a bridge;
each $R_4'$ is H, a substituent, together with $R_2'$ forms a bridge, together with $R_3'$ forms a bridge, or together with $R_5'$ forms a bridge;
q is 0 or 1;
$R_5'$ is H, a substituent, or together with $R_4'$ forms a bridge;
Bx is a nucleobase;
T' is a removable protecting group;
LL is a linking moiety; and
SS is a bead of the invention as described herein;
the method comprising:
a) providing a bead of the invention;
b) attaching one end of a bifunctional linker LL to a functional group of the bead; and
c) reacting the other end of the bifunctional linker LL with a compound of Formula IV:

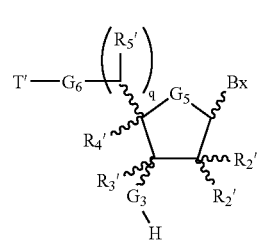

IV to form the compound of Formula I. In some embodiments, $G_3$, $G_5$ and $G_6$ are each O. In further embodiments, at least one $R_2'$ is H, and $R_3'$ and $R_4'$ are each H.

Also provided in accordance with the present invention are processes for the preparation of a compound of Formula II:

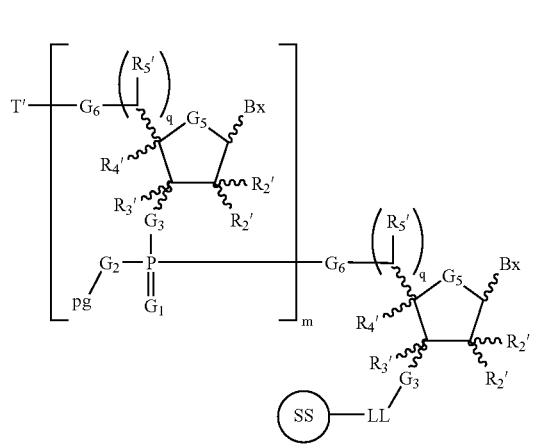

II wherein:
  m is an integer from 1 to about 100;
  each $G_1$ is O or S;
  each $G_2$ is OH or SH;
  each $G_3$ is O, S, $CH_2$, or NH;
  each $G_5$ is O, S, $CH_2$, CFH, $CF_2$, or —CH=CH—;
  each $R_2'$ is H, OH, O-rg, wherein rg is a removable protecting group, a 2'-substituent, or together with $R_4'$ forms a bridge;
  each $R_3'$ is H, a substituent, or together with $R_4'$ forms a bridge;
  each $R_4'$ is H, a substituent, together with $R_2'$ forms a bridge, together with $R_3'$ forms a bridge, or together with $R_5'$ forms a bridge;
  each q is 0 or 1;
  each $R_5'$ is H, a substituent, or together with $R_4'$ forms a bridge;
  each $G_6$ is O, S, $CH_2$ or NH;
  each Bx is a nucleobase;
  T' is H or a protecting group;
  LL is a linking moiety or a single bond; and
  SS is a bead of the invention as described herein; the method comprising:
  a) providing a compound of Formula I:

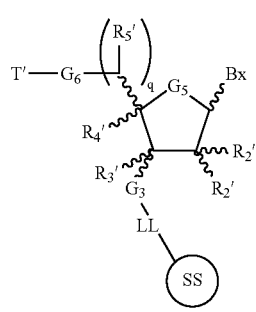

I wherein T' is a removable protecting group;
  b) removing the protecting group T' to form a deprotected support bound nucleoside;
  c) reacting the deprotected support bound nucleoside of step (b) with a protected nucleoside amidite or Formula V:

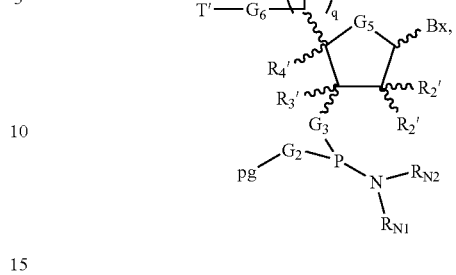

V wherein $R_{N1}$ and $R_{N2}$ are alkyl having from one to six carbon atoms, to form a phosphite compound of Formula VI:

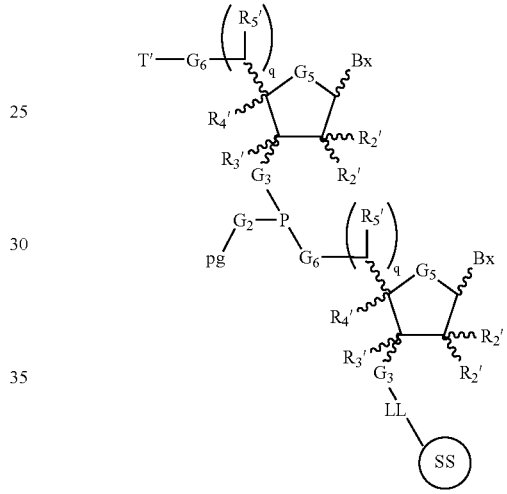

VI d) oxidizing or sulfurizing the phosphate of Formula VI to form a compound of Formula II, wherein m is 1;
  e) optionally capping unreacted nucleosides; and
  f) optionally repeating steps (b)-(e) one or more times.

In some embodiments, each $G_3$, $G_5$ and $G_6$ is O. In further embodiments, at least one each pair of vicinal $R_2'$ groups is H, and each $R_3'$ and each $R_4'$ is H. In some further embodiments, the process further includes cleaving the resulting oligonucleotide from the solid support.

The polymeric beads of the invention are also useful for the preparation of amide-linked oligomers, for example proteins, peptides, and their analogs, and amide linked nucleobase- or nucleobase analog-bearing oligomers, such as peptide nucleic acids. As used herein, the term "amino acid" refers to a monomeric species having both an amino group and a carboxyl group. Thus, "amino acids" include the naturally occurring α-amino acids as occur in peptides and proteins, their analogs, other naturally occurring amino acids such as γ-amino butyric acid, and other non-naturally occurring amino acids from which oligomeric compounds can be prepared. Accordingly, in some embodiments, the invention provides processes for preparing an oligomer comprising amino acid monomers, the method comprising:

(a) providing a polymer substrate, said polymer substrate has the formula SS-LL-ZZ, wherein SS is a polymeric bead of the invention, LL is an optional linker, and ZZ is a chemical group capable of forming an anchoring linkage with either the carboxyl group or the amino group of an amino acid;

(b) coupling a first amino acid synthon to said substrate through either the carboxyl group or the amino group of the amino acid, said synthon having a protecting group at the uncoupled carboxyl group or amino group thereof;

(c) removing the protecting group from the coupled first amino acid to generate a free amino or carboxyl group; and (d) reacting the free amino or carboxyl group with a second amino acid synthon, to form a peptide chain. In further embodiments, the processes further comprise the steps of:

(e) removing the protecting group from the second amino acid synthon to generate a terminal free amino or carboxyl group on said peptide chain; and (f) reacting said free amino or carboxyl group on said peptide chain with a further protected amino acid synthon to lengthen said peptide chain.

In some embodiments where longer species are desired, steps e and f are performed a plurality of times. When the desired sequence is achieved, the anchoring linkage is then cleaved without substantially degrading the assembled chain.

In some preferred embodiments, the amino acid synthons are naturally occurring amino acids, their analogs, or peptide nucleic acids.

In some further embodiments, the invention provides processes for preparing a compound of Formula X:

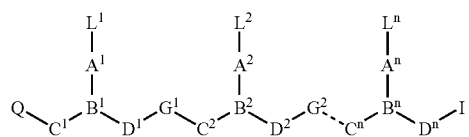

wherein:
n is at least 2,
each of $L^1$-$L^n$ is independently selected from the group consisting of hydrogen, hydroxy, ($C_1$-$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$-$L^n$ being a naturally occurring nucleobase, a non-naturally occurring nucleobase, a DNA intercalator, or a nucleobase-binding group;

each of $C^1$-$C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, ($C_2$-$C_6$)alkyl, aryl, aralkyl, heteroaryl, hydroxy, ($C_1$-$C_6$)alkoxy, ($C_1$-$C_6$)alkylthio, $NR^3R^4$ and $SR^5$, where $R^3$ and $R^4$ are as defined above, and $R^5$ is hydrogen, ($C_1$-$C_6$)alkyl, hydroxy-, alkoxy-, or alkylthio-substituted ($C_1$-$C_6$)alkyl, or $R^6$ and $R^7$ taken together complete an alicyclic or heterocyclic system;

each of $D^1$-$D^n$ is $(CR^6R^7)_z$ where $R^6$ and $R^7$ are as defined above;

each of y and z is zero or an integer from 1 to 10, the sum y+z being greater than 2 but not more than 10;

each of $G^1$-$G^{n-1}$ is —$NR^3CO$—, —$NR^3CS$—, —$NR^3SO$— or —$NR^3SO_2$—, in either orientation, where $R^3$ is as defined above;

each of $A^1$-$A^n$ and $B^1$-$B^n$ are selected such that:

(a') A is a group of formula (IIa), (IIb) or (IIc), and B is N or $R^3N^+$, provided that at least one A is a group of formula (IIc); or (b') A is a group of formula (IId) and B is CH; or (c') A is a group of formula (IIa) or (IIb) and B is N or $R^3N^+$, provided at least one of y or z is not 1 or 2;

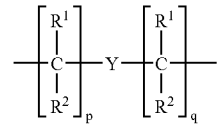

(IIa)

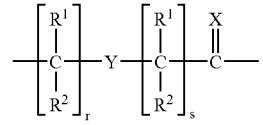

(IIb)

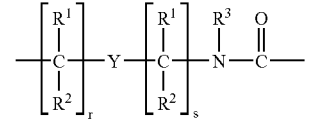

(IIc)

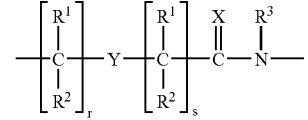

(IId)

where:
X is O, S, Se, $NR^3$, $CH_2$ or $C(CH_3)_2$;
Y is a single bond, O, S or $NR^4$;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, ($C_1$-$C_4$)alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, ($C_1$-$C_4$)alkyl, hydroxy- or alkoxy- or alkylthio-substituted ($C_1$-$C_4$)alkyl, hydroxy, alkoxy, alkylthio and amino;
Q is —$CO_2H$, —$CONR'R''$, —$SO_3H$ or —$SO_2NR'R''$ or an activated derivative of —$CO_2H$ or —$SO_3H$; and
I is —$NHR'''R''''$ or —$NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers;

the process comprising the steps of:
(a) providing a polymer substrate, said polymer substrate having the formula SS-LL-ZZ, wherein SS is a polymeric bead of the invention as described herein, LL is a linker, and ZZ is a chemical group capable of forming an anchoring linkage with an amino acid;

(b) coupling said polymer substrate with a first amino acid through said anchoring linkage, said first amino acid having formula (XX):

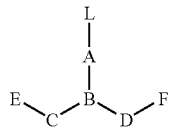

(XX)

wherein:

L is selected from the group consisting of naturally occurring nucleobases, non-naturally occurring nucleobases, aromatic moieties, DNA intercalators, nucleobase-binding groups, heterocyclic moieties, and reporter ligands, wherein amino groups are, optionally, protected by amino protecting groups;

each C is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where $R^3$ and $R^4$ are as defined above, and $R^5$ is hydrogen, $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;

each D is $(CR^6R^7)$ where $R^6$ and $R^7$ are as defined above;

each of y and z is zero or an integer from 1 to 10, the sum y+z being greater than 2 but not more than 10;

A and B are selected such that:
(a') A is a group of formula (IIc) and B is N or $R^3N^+$; or
(b') A is a group of formula (IId) and B is CH; or
(c') A is a group of formula (IIa) or (IIb) and B is N or $R^3N^+$, provided at least one of y or z is not 1 or 2;

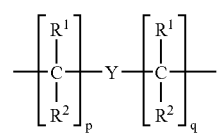 (IIa)

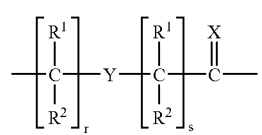 (IIb)

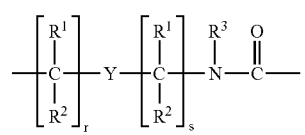 (IIc)

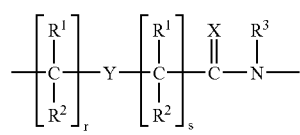 (IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

each E is COOH, CSOH, SOOH, $SO_2OH$ or an activated or protected derivative thereof; and each F is $NHR^3$ or $NPgR^3$, where $R^3$ is as defined above, and Pg is an amino protecting group;

(c) removing said amino protecting group from said coupled first amino acid to generate a free amino group; and (d) reacting said free amino group with a second amino acid having formula (XX) to form a peptide chain. In some embodiments, the processes further include the steps of:

(e) removing said amino protecting group from said second amino acid to generate a terminal free amino group on said peptide chain; and (f) reacting said free amino group on said peptide chain with a further amino acid having formula (XX) to lengthen said peptide chain. In some embodiments, steps e and f are performed a plurality of times. Some further embodiments further include removing at least one protecting group remaining on the amino acid moieties of the peptide chain. Preferably, when the synthesis of the desired sequence is complete, the anchoring linkage is cleaved from the support without substantially degrading said assembled chain.

In some embodiments of the processes above, the chemical group capable of forming said anchoring linkage is chloro-, bromo- and iodo-substituted alkyl, amino-substituted alkyl, amino and aryl-substituted alkyl, amino- and alkylaryl-substituted alkyl, hydroxy-substituted alkyl, or a derivative thereof having a spacer group that can be cleaved substantially without degradation of said polypeptide. In some embodiments, chloro-substituted alkyl is chloromethyl, amino-substituted alkyl is aminomethyl, amino- and alkyl-substituted aryl is α-aminobenzyl, amino- and alkylaryl-substituted alkyl is selected from the group consisting of α-amino-3- and α-amino-4-methylbenzyl, and hydroxy-substituted alkyl is hydroxymethyl. In some further embodiments, the chemical group is derived from an amino-containing moiety selected from amino-substituted alkyl, amino- and aryl substituted alkyl and amino- and alkylaryl-substituted alkyl; and the chemical group includes a spacer group derived from the group consisting of 4-(haloalkyl) aryl-lower alkanoic acids, Boc-aminoacyl-4-(oxymethyl) aryl-lower alkanoic acids, N-Boc-p-acylbenzhydrylamines, N-Boc-4'-(lower alkyl)-p-acylbenzhydrylamines, N-Boc-4'-(lower alkoxy)-p-acylbenzhydrylamines, and 4-hydroxymethylphenoxy-lower alkanoic acids.

In some embodiments, the compound X has the formula:

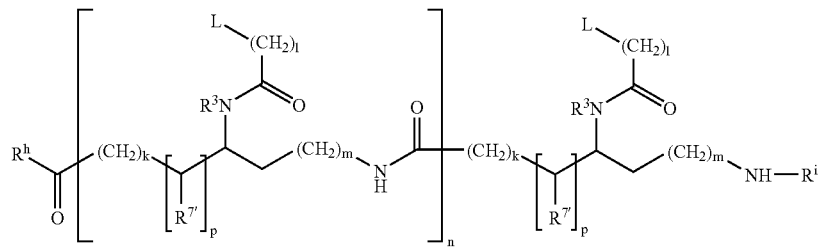

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer from 1 to 60, each k, l, and m is, independently, zero or an integer from 1 to 5;

each p is zero or 1;

$R^h$ is OH, $NH_2$ or —$NHLysNH_2$; and $R^i$ is H or $COCH_3$.

In further embodiments, the compound X has the formula:

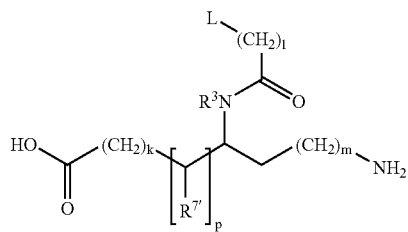

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer from 1 to 60, each k, l, and m is, independently, zero or an integer from 1 to 5;

each p is zero or 1;

$R^h$ is OH, $NH_2$ or —$NHLysNH_2$; and $R^i$ is H or $COCH_3$.

In further embodiments, said amino acid having formula (XX) has the formula:

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids; and each k, l, and m is, independently, zero or an integer from 1 to 5.

In still further embodiments, said amino acid having formula (XX) has the formula:

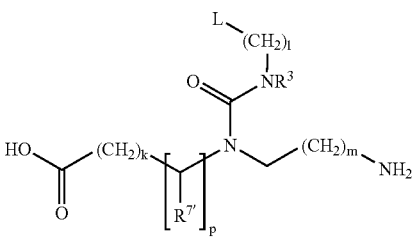

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids; and each k, l, and m is, independently, zero or an integer from 1 to 5.

In one embodiment, the invention provides crosslinked, functionalized polystyrene beads, having excellent properties, such as exceptional uniformity in bead size distribution, pore size, density, swelling properties and/or tolerance to solvents and reagents typically used in oligomer synthesis. In some preferred embodiments, the beads have superior loading characteristics. In some preferred embodiments, the beads have a loading capability of at least about 50 μmole per gram of bead; of at least about 100 μmole per gram of bead; of at least about 150 μmole per gram of bead; of at least about 200 μmole per gram of bead; of at least about 250 μmole per gram of bead; of at least about 300 μmole per gram of bead; of at least about 350 μmole per gram of bead; of at least about 400 μmole per gram of bead; or at least about 450 μmole per gram of bead. In some embodiments, the bead has a loading capability of from about 100 μmole per gram of bead to about 350 μmole per gram of bead.

In some embodiments, inventive beads have a mean particle size in the range of about 1 μm to about 1000 μm. In preferred embodiments, inventive beads have a mean particle size in the range of about 5 μm to about 500 μm. In especially preferred embodiments, inventive beads have a mean particle size in the range of about 10 μm to about 300 μm.

The polymeric bead supports of the present invention are amenable to the preparation of any of the wide variety of monomeric and oligomeric molecules that are synthesized by combinatorial methods. It is now widely appreciated that combinatorial libraries are useful per se and that such libraries and compounds comprising them have great commercial importance. Indeed, a branch of chemistry has developed to exploit the many commercial aspects of combinatorial libraries. In order to maximize the advantages of each classical combinatorial approach, new strategies for combinatorial deconvolution have been developed independently by several groups. Selection techniques have been used with libraries of peptides (Geysen et al., *J. Immun. Meth.*, 1987, 102, 259; Houghten et al., *Nature*, 1991, 354, 84; Owens et al., *Biochem. Biophys. Res. Commun.*, 1991, 181, 402; Doyle, PCT WO 94/28424; Brennan, PCT WO 94/27719); nucleic acids (Wyatt et al., *Proc. Natl. Acad. Sci. U.S.A.*, 1994, 91, 1356; Ecker et al., *Nucleic Acids Res.*, 1993, 21, 1853); nonpeptides and small molecules (Simon et al., *Proc. Natl. Acad. Sci. U.S.A.*, 1992, 89, 9367; Zuckermann et al., *J. Am. Chem. Soc.*, 1992, 114, 10646; Bartlett et al., WO 91/19735; Ohlmeyer et al., *Proc. Natl. Acad. Sci. U.S.A.*, 1993, 90, 10922; DeWitt et al., *Proc. Natl. Acad. Sci. U.S.A.*, 1993, 90, 6909; Cody et al., U.S. Pat. No. 5,324,483; Houghten et al., PCT WO 94/26775; Ellman, U.S. Pat. No. 5,288,514; Still et al., WO 94/08051; Kauffman et al., PCT WO 94/24314; Carell et al., *Angew. Chem. Int. Ed. Engl.*, 1994, 33, 2059; Carell et al., *Angew. Chem. Int. Ed. Engel.*, 1994, 33, 2061; Lebl et al., WO 94/28028). Each of the preceding is hereby incorporated by reference in its entirety. A review of the above references reveals that the most advanced of these techniques are those for the selection of peptides and nucleic acids.

The majority of the techniques reported to date involve iterative synthesis and screening of increasingly simplified subsets of oligomers such as peptides and oligonucleotides. Monomers or sub-monomers that have been utilized include amino acids, amino acid-like molecules, i.e. carbamate precursors, and nucleotides, both of which are bifunctional. Utilizing these techniques, libraries have been assayed for activity in either cell-based assays, or for binding and/or inhibition of purified protein targets.

Some combinatorial approaches utilize a multifunctional scaffold bearing multiple diversity sites, and derivatizing these sites with varied building blocks to form libraries of diverse small molecule compounds. Libraries may be generated such that each individual compound may be synthesized and isolated separately, or synthesized and used as a mixture of several desirable compounds. A mixture of compounds may be obtained by using a mixture of scaffolds and/or building blocks.

The diversity of a combinatorial library is represented by the inherent physical and chemical properties of each scaffold and building block used, the number of different building blocks used during each derivatization step, the physical and chemical properties of the bonds arising from the derivatization chemistry, and the interactions of the scaffold and building block chemistries. Taken together, these interactions provide a unique conformation for each individual compound in the combinatorial library.

The polymeric bead supports of the present invention are amenable to the preparation of any of the wide variety of monomeric and oligomeric molecules that are synthesized by such combinatorial methods. These include conventional small molecule drugs, and larger species such as oligomeric peptidomimetics, peptoids, and nucleotides, as well as oligomeric molecules derived from other preorganized or rigid scaffolds.

For example, acids, amines and amino acids are classes of building blocks that have been recognised to be of tremendous utility in combinatorial chemistry because of their reactivity with a variety of functional groups and the availability of large numbers of such compounds of diverse structures from commercial sources. Amino acids, for example, have been extensively used in the synthesis of small molecule combinatorial libraries. The use of amino acids as key building blocks in the construction of substituted heterocycle libraries has been practiced by several groups for exploring known pharmacophores, in cyclic ureas and in 'prospecting libraries' (Bunin and Ellman, *J. Am. Chem. Soc.*, 1992, 114, 10997; DeWitt et al., *Proc. Natl. Acad. Sci. USA*, 1993, 90, 6909; Nefzi, et al., *Tetrahedron Lett.*, 1997, 38, 931; Bartlett, et al., *Book of Abstracts*, 213th American Chemical Society National Meeting, San Francisco, 1997, American Chemical Society, Washington D.C., ORGN-273).

In some combinatorial procedures, the scaffold possess a plurality of masked (i.e., protected) functional groups (diversity sites). All the diversity sites are protected or masked in such a fashion that the protection and deprotection schemes are orthogonal in nature, i.e. one may be deprotected selectively without affecting the integrity of any of the other masking groups. This, allows for selective functionalization of individual diversity sites as the scaffolds are attached or constructed during synthesis of the oligomeric or monomeric, compounds. Alternatively, this also allows for the simultaneous reaction of multiple diversity sites, if so desired.

The diversity sites may be combinatorialized with diverse building blocks. Sites that are available for combinatorializing include the reactive amino and hydroxy groups. Derivatization of scaffolds at diversity sites is achieved using a variety of building blocks that include, but are not limited to, carboxylic acids, acid halides, anhydrides, sulfonic acids, sulfonyl halides, isocyanates, isothiocyanates, ketones, aldehydes, amines, and amino acids.

In some embodiments, the present invention provides for the addition of functional groups onto a monocyclic or bicyclic scaffold which is attached to a solid support of the invention. The preparation of the combinatorial libraries begins with a monocyclic or bicyclic scaffold attached to the solid support directly, or through a linker stable to the synthesis conditions, but cleavable to release the compound into solution at the end of the synthesis. Preferred linkers include esters, particularly those derived from succinic acid. Alternatively, the scaffolds can be coupled to a constant moiety attached to the support, such as DMT, ethylene glycol or a similar diol.

The scaffolds can be uniform, or a structurally diverse set of monocyclic and/or bicyclic ring systems which give different relative orientations of the functional groups and the pendant, diverse substituents. Additional combinatorial sites may be present on the scaffolds in the form of protected hydroxy or amino groups or other masked functional groups which may be selectively reacted with building blocks when desired. The scaffolds and building blocks used in the combinatorial library bear varied functional groups which, taken together, provide diverse properties ("diversity") to the resulting library members. These functional groups include hydrogen-bond donors and acceptors, ionic moieties, polar moieties, hydrophobic moieties, aromatic centers, and electron-donors and acceptors. Together, the properties of the individual scaffolds and building blocks contribute to the uniqueness of the individual compounds in which they are found. Thus, a library of such compounds would have a myriad of properties, i.e., "diversity." Collectively, the properties of the individual scaffold and building blocks, which together form an individual library compound, contribute to the uniqueness of the compound and impart certain characteristics thereto for interaction with cellular, enzymatic or nucleic acid target sites.

As used herein, the term oligonucleotide has the meaning of an oligomer having m subunits embraced within the brackets [ ] of the formula:

Oligonucleotide

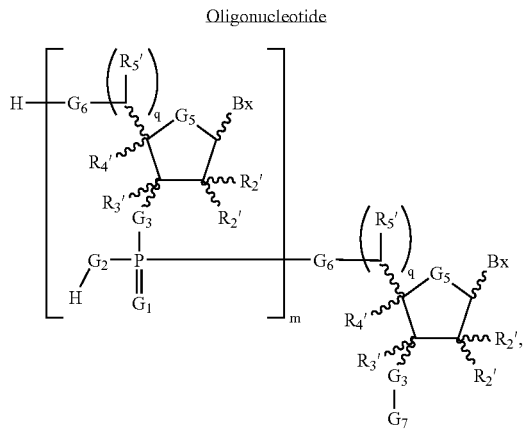

wherein the other variables are defined above, and are described in more detail hereinafter. It is to be understood that, although the oligonucleotide to be made is depicted in a single stranded conformation, it is common for oligonucleotides to be used in a double stranded conformation. For example, in the antisense method referred-to commonly as siRNA, two strands of RNA or RNA-like oligonucleotide are prepared and annealed together, often with a two-nucleotide overlap at the ends. Thus, the present invention contemplates manufacture of both single- and double-stranded oligonucleotides.

Nucleobases

The nucleobases Bx may be the same or different, and include naturally occurring nucleobases adenine (A), guanine (G), thymine (T), uracil (U) and cytosine (C), as well as modified nucleobases. Modified nucleobases include heterocyclic moieties that are structurally related to the naturally-occurring nucleobases, but which have been chemically modified to impart some property to the modified nucleobase that is not possessed by naturally-occurring nucleobases. The term "nucleobase," as used herein, is intended to by synonymous with "nucleic acid base or mimetic thereof." In general, a nucleobase is any substructure that contains one or more atoms or groups of atoms capable of hydrogen bonding to a base of an oligonucleotide.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* pages 858-859, Kroschwitz, J. I., ed. John Wiley & Sons, 1990, those disclosed by Englisch et al., *Angewandte Chemie,* International Edition, 1991, 30, 613, and those disclosed by Sanghvi, Y. S., Chapter 15, *Antisense Research and Applications,* pages 289-302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications,* CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

In some embodiments of the invention, oligomeric compounds, e.g. oligonucleotides, are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

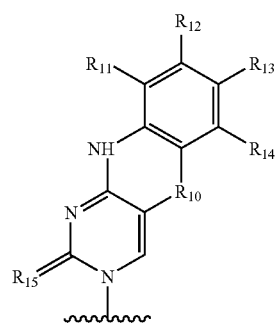

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides,* 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligo-nucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety.

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds.

This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

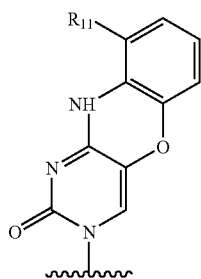

Wherein R$_{11}$ includes (CH$_3$)$_2$N—(CH$_2$)$_2$—O—; H$_2$N—(CH$_2$)$_3$—; Ph—CH$_2$—O—C(=O)—N(H)—(CH$_2$)$_3$—; H$_2$N—; Fluorenyl-CH$_2$—O—C(=O)—N(H)—(CH$_2$)$_3$—; Phthalimidyl-CH$_2$—O—C(=O)—N(H)—(CH$_2$)$_3$—; Ph—CH$_2$—O—C(=O)—N(H)—(CH$_2$)$_2$—O—; Ph—CH$_2$—O—C(=O)—N(H)—(CH$_2$)$_3$—O—; (CH$_3$)$_2$N—N(H)—(CH$_2$)$_2$—O—; Fluorenyl-CH$_2$—O—C(=O)—N(H)—(CH$_2$)$_2$—O—; Fluorenyl-CH$_2$—O—C(=O)—N(H)—(CH$_2$)$_3$—O—; H$_2$N—(CH$_2$)$_2$—O—CH$_2$—; N$_3$—(CH$_2$)$_2$—O—CH$_2$—; H$_2$N—(CH$_2$)$_2$—O—, and NH$_2$C(=NH)NH—.

Also disclosed are tricyclic heterocyclic compounds of the formula:

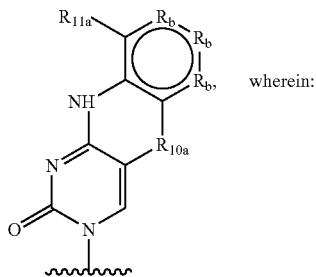

wherein:

R$_{10a}$ is O, S or N—CH$_3$; R$_{11a}$ is A(Z)$_{x1}$, wherein A is a spacer and Z independently is a label bonding group bonding group optionally bonded to a detectable label, but R$_{11a}$ is not amine, protected amine, nitro or cyano; X1 is 1, 2 or 3; and R$_b$ is independently —CH=, —N=, —C(C$_{1-8}$ alkyl)= or —C(halogen)=, but no adjacent R$_b$ are both —N=, or two adjacent R$_b$ are taken together to form a ring having the structure:

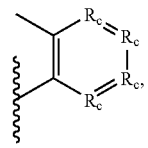

where R$_c$ is independently —CH=, —N=, —C(C$_{1-8}$ alkyl)= or —C(halogen)=, but no adjacent R$_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20 mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

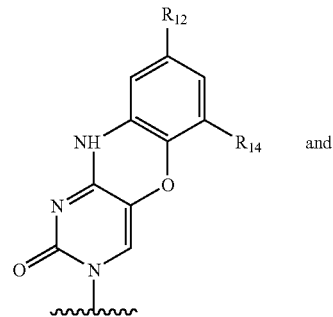 and

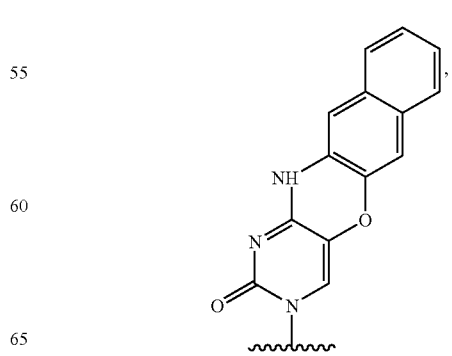

wherein $R_{14}$ is $NO_2$ or both $R_{14}$ and $R_{12}$ are independently —$CH_3$. The synthesis of these compounds is dicslosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety.

Further tricyclic heterocyclic compounds amenable to the present invention also disclosed in the "257, 177 and 269" Patents include those having the formula:

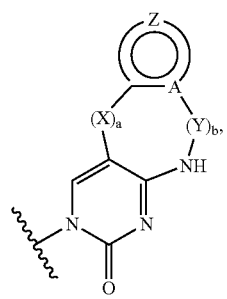

wherein a and b are independently 0 or 1 with the total of a and b being 0 or 1; A is N, C or CH; X is S, O, C=O, NH or $NCH_2$, $R^6$; Y is C=O; Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 nonbridging ring carbon atom is substituted with $R^{20}$ or =O; or Z is taken together with A to form an aryl ring structure comprising 6 ring atoms wherein the aryl ring carbon atoms are unsubstituted with other than H or at least 1 nonbridging ring carbon atom is substituted with $R^6$ or =O; $R^6$ is independently H, $C_{1-6}$ alkyl, $C_{2-6}$ alkenyl, $C_{2-6}$ alkynyl, $NO_2$, $N(R^3)_2$, CN or halo, or an $R^6$ is taken together with an adjacent Z group $R^6$ to complete a phenyl ring; $R^{20}$ is, independently, H, $C_{1-6}$ alkyl, $C_{2-6}$ alkyl, $C_{2-6}$ alkenyl, $C_{2-6}$ alkynyl, $NO_2$, $N(R^{21})_2$, CN or halo, or an $R^{20}$ is taken together with an adjacent $R^{20}$ to complete a ring containing 5 or 6 ring atoms, and tautomers, solvates and salts thereof; $R^{21}$ is, independently, H or a protecting group; $R^3$ is a protecting group or H; and tautomers, solvates and salts thereof.

More specific examples of bases included in the "257, 177 and 269" Patents are compounds of the formula:

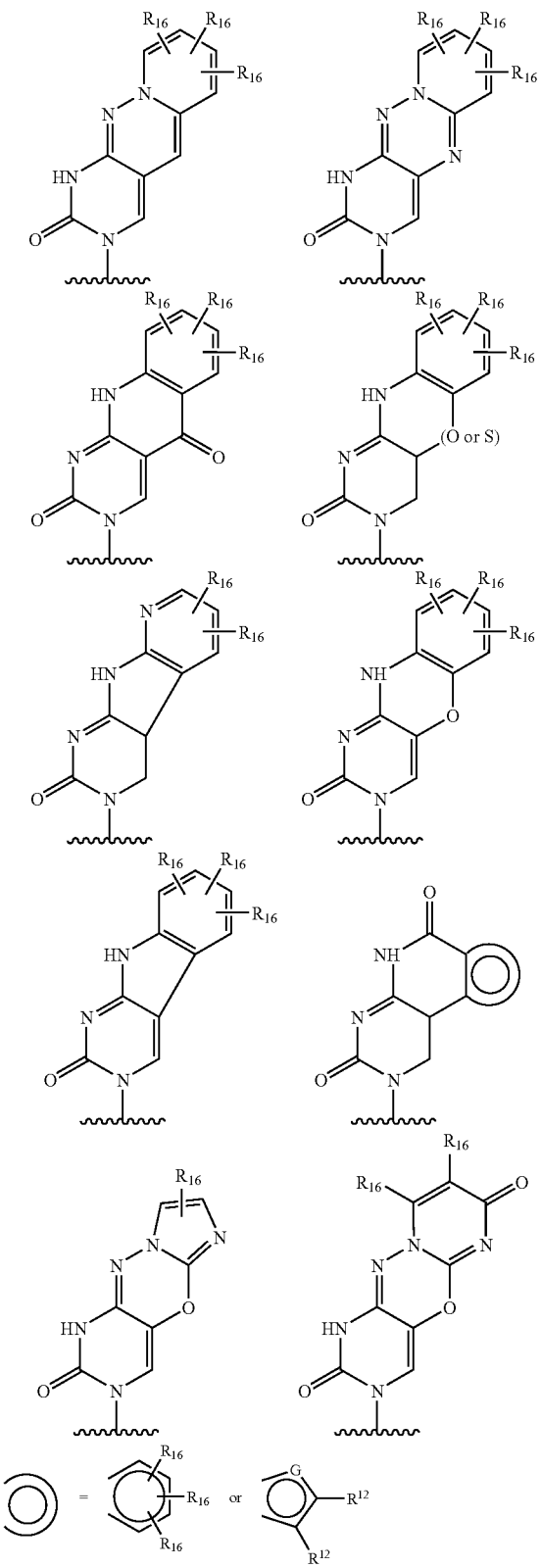

wherein each $R_{16}$, is, independently, selected from hydrogen and various substituent groups. Further polycyclic base moieties having the formula:

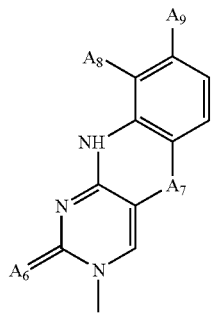

wherein: $A_6$ is O or S; $A_7$ is $CH_2$, N—$CH_3$, O or S; each $A_8$ and $A_9$ is hydrogen or one of $A_8$ and $A_9$ is hydrogen and the other of $A_8$ and $A_9$ is selected from the group consisting of:

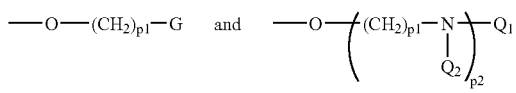

wherein: G is —CN, —$OA_{10}$, —$SA_{10}$, —N(H)$A_{10}$, —ON(H)$A_{10}$ or —C(=NH)N(H)$A_{10}$; $Q_1$ is H, —$NHA_{10}$, —C(=O)N(H)$A_{10}$, —C(=S)N(H)$A_{10}$ or —C(=NH)N(H)$A_{10}$; each $Q_2$ is, independently, H or Pg; $A_{10}$ is H, Pg, substituted or unsubstituted $C_1$-$C_{10}$ alkyl, acetyl, benzyl, —$(CH_2)_{p3}NH_2$, —$(CH_2)_{p3}N(H)Pg$, a D or L α-amino acid, or a peptide derived from D, L or racemic α-amino acids; Pg is a nitrogen, oxygen or thiol protecting group; each p1 is, independently, from 2 to about 6; p2 is from 1 to about 3; and p3 is from 1 to about 4; are disclosed in U.S. patent application Ser. No. 09/996,292 filed Nov. 28, 2001, which is commonly owned with the instant application, and is herein incorporated by reference.

Sugars and Sugar Substituents

The sugar moiety:

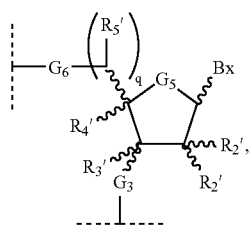

wherein each dashed line (----) indicates a point of attachment to an adjacent phosphorus atom, represents the sugar portion of a general nucleoside or nucleotide as embraced by the present invention.

Suitable 2'-substituents corresponding to $R_2'$ include: OH, F, O-alkyl (e.g. O-methyl), S-alkyl, N-alkyl, O-alkenyl, S-alkenyl, N-alkenyl; O-alkynyl, S-alkynyl, N-alkynyl; O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocyloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred 2'-modification includes 2'-methoxyethoxy (2'-O—$CH_2CH_2OCH_3$, also known as 2'-O—(2-methoxyethyl) or 2'-MOE) (Martin et al., *Helv. Chim. Acta*, 1995, 78, 486-504). A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula $I_a$ or $II_a$:

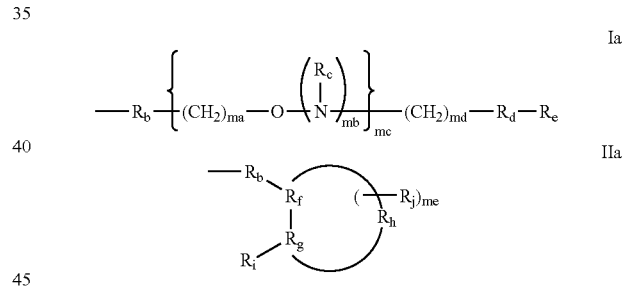

wherein: $R_b$ is O, S or NH; $R_d$ is a single bond, O or C(=O); $R_e$ is $C_1$-$C_{10}$ alkyl, N($R_k$)($R_m$), N($R_k$)($R_n$), N=C($R_p$)($R_q$), N=C($R_p$)($R_r$) or has formula $III_a$;

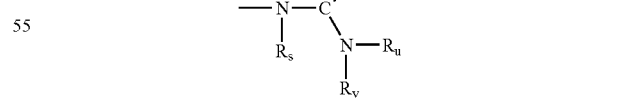

Each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl; or optionally, $R_u$ and $R_v$, together form a phthalimido moiety with the nitrogen atom to which they are attached; each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl; $R_k$ is hydrogen, a nitrogen protecting group or -$R_x$-$R_y$; $R_p$ is hydrogen, a nitrogen protecting group or -$R_x$-$R_y$; $R_x$ is a bond or a linking moiety; $R_y$ is a chemical functional group, a conjugate group or a solid support medium medium; each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester; or $R_m$ and $R_n$, together, are a nitrogen protecting group, are joined in a ring structure that optionally includes an additional heteroatom selected from N and O or are a chemical functional group; $R_i$ is $OR_z$, $SR_z$, or $N(R_z)_2$; each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$; $R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN; $m_a$ is 1 to about 10; each mb is, independently, 0 or 1; mc is 0 or an integer from 1 to 10; md is an integer from 1 to 10; me is from 0, 1 or 2; and provided that when mc is 0, md is greater than 1.

Representative substituents groups of Formula I are disclosed in U.S. Pat. No. 6,172,209. Representative cyclic substituent groups of Formula II are disclosed in U.S. Pat. No. 6,271,358.

Particularly useful sugar substituent groups include O[(CH$_2$)$_g$O]$_h$CH$_3$, O(CH$_2$)$_g$OCH$_3$, O(CH$_2$)$_g$NH$_2$, O(CH$_2$)$_g$CH$_3$, O(CH$_2$)$_g$ONH$_2$, and O(CH$_2$)$_g$ON[(CH$_2$)$_g$CH$_3$)]$_2$, where g and h are from 1 to about 10.

Some particularly useful oligomeric compounds of the invention contain at least one nucleoside having one of the following substituent groups: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—CH$_2$CH$_2$OCH$_3$, also known as 2'-O—(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. patent application Ser. No. 09/344,260, filed Jun. 25, 1999, now U.S. Pat. No. 6,567,752, issued on Jun. 10, 2003, entitled "Aminooxy-Functionalized Oligomers"; and U.S. patent application Ser. No. 09/370,541, filed Aug. 9, 1999, now U.S. Pat. No. 6,639,062, issued on Oct. 28, 2003, entitled "Aminooxy-Functionalized Oligomers and Methods for Making Same;" hereby incorporated by reference in their entirety.

Other particularly advantageous 2'-modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053, 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, now U.S. Pat. No. 5,859,221, issued on Jan. 12, 1999, also herein incorporated by reference.

Representative guanidino substituent groups that are shown in formula III and IV are disclosed in co-owned U.S. patent application Ser. No. 09/349,040, entitled "Functionalized Oligomers", filed Jul. 7, 1999, now U.S. Pat. No. 6,593,466, issued on Jul. 15, 2003.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, now WIPO publication number 2000/08044 and published on Feb. 17, 2000, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

While the present invention may be adapted to produce oligonucleotides for any desired end use (e.g. as probes for us in the polymerase chain reaction), one preferred use of the oligonucleotides is in antisense therapeutics. One mode of action that is often employed in antisense therapeutics is the so-called RNAse H mechanism, whereby a strand of DNA is introduced into a cell, where the DNA hybridizes to a strand of RNA. The DNA-RNA hybrid is recognized by an endonuclease, RNAse H, which cleaves the RNA strand. In normal cases, the RNA strand is messenger RNA (mRNA), which, after it has been cleaved, cannot be translated into the corresponding peptide or protein sequence in the ribosomes. In this way, DNA may be employed as an agent for modulating the expression of certain genes.

It has been found that by incorporating short stretches of DNA into an oligonucleotide, the RNAse H mechanism can be effectively used to modulate expression of target peptides or proteins. In some embodiments of the invention, an oligonucleotide incorporating a stretch of DNA and a stretch of RNA or 2'-modified RNA can be used to effectively modulate gene expression. In preferred embodiments, the oligonucleotide comprises a stretch of DNA flanked by two stretches of 2'-modified RNA. Preferred 2'-modifications include 2'-MOE as described herein.

The ribosyl sugar moiety has also been extensively studied to evaluate the effect its modification has on the properties of oligonucleotides relative to unmodified oligonucleotides. The 2'-position of the sugar moiety is one of the most studied sites for modification. Certain 2'-substituent groups have been shown to increase the lipohpilicity and enhance properties such as binding affinity to target RNA, chemical stability and nuclease resistance of oligonucleotides. Many of the modifications at the 2'-position that show enhanced binding affinity also force the sugar ring into the $C_3$-endo conformation.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

Various synthetic modifications have been proposed to increase nuclease resistance, or to enhance the affinity of the antisense strand for its target mRNA (Crooke et al., *Med. Res. Rev.*, 1996, 16, 319-344; De Mesmaeker et al., *Acc. Chem. Res.*, 1995, 28, 366-374). A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability.

RNA exists in what has been termed "A Form" geometry while DNA exists in "B Form" geometry. In general, RNA:RNA duplexes are more stable, or have higher melting temperatures (Tm) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2=hydroxyl in RNA biases the sugar toward a C3=endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2=hydroxyl groups of RNA can form a network of water mediated hydrogen bonds that help stabilize the RNA duplex (Egli et al., *Biochemistry*, 1996, 35, 8489-8494).

DNA:RNA hybrid duplexes, however, are usually less stable than pure RNA:RNA duplexes and, depending on their sequence, may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of a DNA:RNA hybrid a significant aspect of antisense therapies, as the proposed mechanism requires the binding of a modified DNA strand to a mRNA strand. Ideally, the antisense DNA should have a very high binding affinity with the mRNA. Otherwise, the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2=-methoxyethoxy (MOE, 2'-OCH$_2$CH$_2$OCH$_3$) side chain (Baker et al., *J. Biol. Chem.*, 1997, 272, 11944-12000; Freier et al., *Nucleic Acids Res.*, 1997, 25, 4429-4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429-4443). 2=-O-Methoxyethyl-substituted oligonucleotides also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, they display improved RNA affinity and higher nuclease resistance. Chimeric oligonucleotides with 2=-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE substituted oligonucleotide is presently being investigated in clinical trials for the treatment of CMV retinitis.

LNAs (oligonucleotides wherein the 2' and 4' positions are connected by a bridge) also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

LNAs in which the 2'-hydroxyl group is linked to the 4' carbon atom of the sugar ring thereby forming a 2'-C,4'-C-oxymethylene linkage thereby forming a bicyclic sugar moiety. The linkage may be a methelyne (—$CH_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Other preferred bridge groups include the 2'-deoxy-2'-$CH_2OCH_2$-4' bridge.

Alternative Linkers

In addition to phosphate diester and phosphorothioate diester linkages, other linkers are known in the art. While the primary concern of the present invention has to do with phosphate diester and phosphorothioate diester oligonucleotides, chimeric compounds having more than one type of linkage, as well as oligomers having non-phosphate/phosphorothioate diester linkages as described in further detail below, are also contemplated in whole or in part within the context of the present invention.

Exemplary non-phosphate/phosphorothioate diester linkages contemplated within the skill of the art include: phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, selenophosphates and boranophosphates. Additional linkages include: thiodiester (—O—C(O)—S—), thionocarbamate (—O—C(O) (NJ)—S—), siloxane (—O—Si(J)$_2$—O—), carbamate (—O—C(O)—NH— and —NH—C(O)—O—), sulfamate (—O—S(O)(O)—N— and —N—S(O)(O)—N—, morpholino sulfamide (—O—S(O)(N(morpholino)-), sulfonamide (—O—$SO_2$—NH—), sulfide (—$CH_2$—S—$CH_2$—), sulfonate (—O—$SO_2$—$CH_2$—), N,N'-dimethylhydrazine (—$CH_2$—N($CH_3$)—N($CH_3$)—), thioformacetal (—S—$CH_2$—O—), formacetal (—O—$CH_2$—O—), thioketal (—S—C(J)$_2$-O—), ketal (—O—C(J)$_2$-O—), amine (—NH—$CH_2$—$CH_2$—), hydroxylamine (—$CH_2$—N(J)-O—), hydroxylimine (—CH=N—O—), and hydrazinyl (—$CH_2$—N(H)—N(H)—).

In each of the foregoing substructures relating to internucleoside linkages, J denotes a substituent group which is commonly hydrogen or an alkyl group or a more complicated group that varies from one type of linkage to another.

In addition to linking groups as described above that involve the modification or substitution of the —O—P—O— atoms of a naturally occurring linkage, included within the scope of the present invention are linking groups that include modification of the 5'-methylene group as well as one or more of the —O—P—O— atoms. Linkages of this type are well documented in the prior art and include without limitation the following: amides (—$CH_2$—$CH_2$—N(H)—C(O)) and —$CH_2$—O—N=CH—;and alkylphosphorus (—C(J)$_2$-P(=O)(OJ)-C(J)$_2$-C(J)$_2$—). J is as described above.

Oligonucleotide Synthesis

Oligonucleotides are generally prepared, as described above, on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support medium can be soluble or insoluble, or may possess variable solubility in different solvents to allow the growing support bound polymer to be either in or out of solution as desired. Traditional support medium such as solid support media are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support medium is intended to include all forms of support known to the art skilled for the synthesis of oligomeric compounds and related compounds such as peptides. Some representative support medium that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support medium, polyethylene glycol PEG's (see Bonora et al., Organic Process Research & Development, 2000, 4, 225-231).

Further support medium amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accomodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell plates have not indicated any limitations of the synthetic efficacy.

Further support medium amenable to the present invention include without limitation particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351, and J. C. S. Perkin I 538 (1981)).

Further support medium amenable to the present invention include without limitation a composite of a resin and another material that is also substantially inert to the organic synthesis reaction conditions employed. One exemplary composite (see Scott, et al., *J. Chrom. Sci.,* 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116). Contiguous solid support media other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA,* 1984, 81, 3998). A "tea bag" containing traditionally-used polymer beads. (Houghten, *Proc. Natl. Acad. Sci. USA,* 1985, 82, 5131). Simultaneous use of two different supports with different densities (Tregear, *Chemistry and Biology of Peptides,* J. Meienhofer, ed., Ann Arbor Sci. Publ., Ann Arbor, 1972 pp. 175-178). Combining of reaction vessels via a manifold (Gorman, *Anal. Biochem.,* 1984, 136, 397). Multicolumn solid-phase synthesis (e.g., Krchnak, et al., *Int. J. Peptide Protein Res.,* 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.,* 1989, 54, 1746). Synthesis of peptides on support medium have also been reported (see, *Synthetic Peptides. A User's Guide,* Gregory A. Grant, Ed. Oxford University Press 1992; U.S. Pat. Nos. 4,415,732; 4,458,066; 4,500,707; 4,668,777; 4,973,679; 5,132,418; 4,725,677 and Re. 34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed., Oligonucleotides and Analogues, a Practical Approach, Oxford University Press, New York (1991).

In general, the phosphorus protecting group (pg) is an alkoxy or alkylthio group or O or S having a β-eliminable group of the formula —$CH_2CH_2$-$G_w$, wherein $G_w$ is an electron-withdrawing group. Suitable examples of pg that are amenable to use in connection with the present invention include those set forth in the Caruthers U.S. Pat. Nos. 4,415,732; 4,458,066; 4,500,707; 4,668,777; 4,973,679; and 5,132,418; and Köster U.S. Pat. Nos. 4,725,677 and Re. 34,069. In general the alkyl or cyanoethyl withdrawing groups are preferred, as commercially available phosphoramidites generally incorporate either the methyl or cyanoethyl phosphorus protecting group.

The method for removal of pg depends upon the specific pg to be removed. The β-eliminable groups, such as those disclosed in the Köster et al. patents, are generally removed in a weak base solution, whereby an acidic β-hydrogen is extracted and the —$CH_2CH_2$-$G_w$ group is eliminated by rearrangement to form the corresponding acrylo-compound $CH_2$=CH-$G_w$. In contrast, an alkyl group is generally removed by nucleophilic attack on the α-carbon of the alkyl group. Such PGs are described in the Caruthers et al. patents, as cited herein.

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent," which is also considered to have the same meaning as "thiation reagent." Oxidation, unless otherwise modified, indicates introduction of oxygen or sulfur, with a concomitant increase in P oxidation state from III to V. Where it is important to indicate that an oxidizing agent introduces an oxygen into a P(III) species to make a P(V) species, the oxidizing agent will be referred to herein is "an oxygen-introducing oxidizing reagent."

Oxidizing reagents for making phosphate diester linkages (i.e. oxygen-introducing oxidizing reagents) under the phosphoramidite protocol have been described by e.g. Caruthers et al. and Köster et al., as cited herein. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Oxidizing reagents for making phosphorothioate diester linkages include phenylacetyldisulfide (PADS), as described by Cole et al. In U.S. Pat. No. 6,242,591. In some embodiments of the invention, the phosphorothioate diester and phosphate diester linkages may alternate between sugar subunits. In other embodiments of the present invention, phosphorothioate linkages alone may be employed. In some embodiments, the thiation reagent may be a dithiuram disulfides. See U.S. Pat. No. 5,166,387 for disclosure of some suitable dithiuram disulfides. It has been surprisingly found that one dithiuram disulfide may be used together with a standard capping reagent, so that capping and oxidation may be conducted in the same step. This is in contrast to standard oxidative reagents, such as Beaucage reagent, which require that capping and oxidation take place in separate steps, generally including a column wash between steps.

The 5'-protecting group bg or T' is a protecting group that is orthogonal to the protecting groups used to protect the nucleobases, and is also orthogonal, where appropriate to 2'-O-protecting groups, as well as to the 3'-linker to the solid support medium. In some embodiments of the invention, the 5'-protecting group is acid labile. In some embodiments according to the invention, the 5'-protecting group is selected from an optionally substituted trityl group and an optionally substituted pixyl group. In some embodiments, the pixyl group is substituted with one or more substituents selected from alkyl, alkoxy, halo, alkenyl and alkynyl groups. In some embodiments, the trityl groups are substituted with from about 1 to about 3 alkoxy groups, specifically about 1 to about 3 methoxy groups. In particular embodiments of the invention, the trityl groups are substituted with 1 or 2 methoxy groups at the 4- and (if applicable) 4'-positions. A particularly acceptable trityl group is 4,4'-dimethoxytrityl (DMT or DMTr).

In the context of the present invention, the term "reagent push" has the meaning of a volume of solvent that is substantially free of any active compound (i.e. reagent, activator, by-product, or other substance other than solvent), which volume of solvent is introduced to the column for the purpose, and with the effect, of pushing a reagent solution onto and through the column ahead of a subsequent reagent solution. A reagent push need not be an entire column volume, although in some cases it may include one or more column volumes. In some embodiments, a reagent push comprises at least the minimum volume necessary to substantially clear reagent, by-products and/or activator from a cross-section of the column immediately ahead of the front formed by the reagent solution used for the immediately subsequent synthetic step. An active compound, whether a reagent, by-product or activator, is considered substantially cleared if the concentration of the compound in a cross-section of the column at which the following reagent solution front is located, is low enough that it does not substantially affect the activity of the following reagent solution. The person skilled in the art will recognize that this the volume of solvent required for a "reagent push" will vary depending upon the solvent, the solubility in the solvent of the reagents, activators, by-products, etc., that are on the column, the amounts of reagents, activators, by-products, etc. that are to be cleared from the column, etc. It is considered within the skill of the artisan to select an appropriate volume for each reagent push, especially with an eye toward the Examples, below.

As used herein, unless "column wash" is otherwise modified, it has the same meaning as "reagent push." In some embodiments of the invention, column wash may imply that at least one column volume is permitted to pass through the column before the subsequent reagent solution is applied to the column. Where a column volume (CV) of the column wash is specified, this indicates that a volume of solvent equivalent to the interior volume of the unpacked column is used for the column wash.

In the context of the present invention, a wash solvent is a solvent containing substantially no active compound that is applied to a column between synthetic steps. A "wash step" is a step in which a wash solvent is applied to the column. Both "reagent push" and "column wash" are included within this definition of "wash step".

A wash solvent may be a pure chemical compound or a mixture of chemical compounds, the solvent being capable of dissolving an active compound.

In some embodiments according to the present invention, a wash solvent used in one of the wash steps may comprise some percentage of acetonitrile, not to exceed 50% v/v.

The sequence of capping and oxidation steps may be reversed, if desired. That is, capping may precede or follow oxidation. Also, with selection of a suitable thiation reagent, the oxidation and capping steps may be combined into a single step. For example, it has been surprisingly found that capping with acetic anhydride may be conducted in the presence of N,N'-dimethyldithiuram disulfide.

Various solvents may be used in the oxidation reaction. Suitable solvents are identified in the Caruthers et al. and Köster et al. patents, cited herein. The Cole et al. patent describes acetonitrile as a solvent for phenylacetyldisulfide. Other suitable solvents include toluene, xanthenes, dichloromethane, etc.

Reagents for cleaving an oligonucleotide from a support are set forth, for example, in the Caruthers et al. and Köster et al. patents, as cited herein. It is considered good practice to cleave oligonucleotide containing thymidine (T) nucleotides in the presence of an alkylated amine, such as triethylamine, when the phosphorus protecting group is O—CH$_2$CH$_2$CN, because this is now known to avoid the creation if cyano-ethylated thymidine nucleotides (CNET). Avoidance of CNET adducts is described in general in U.S. Pat. No. 6,465,628, which is incorporated herein by reference, and especially the Examples in columns 20-30, which are specifically incorporated by reference.

The oligonucleotide may be worked up by standard procedures known in the art, for example by size exclusion chromatography, high performance liquid chromatography (e.g. reverse-phase HPLC), differential precipitation, etc. In some embodiments according to the present invention, the oligonucleotide is cleaved from a solid support medium while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

The 5'-hydroxyl protecting groups may be any groups that are selectively removed under suitable conditions. In particular, the 4,4'-dimethoxytriphenylmethyl (DMT) group is a favored group for protecting at the 5'-position, because it is readily cleaved under acidic conditions (e.g. In the presence of dichlroacetic acid (DCA), trichloroacetic acid (TCA), or acetic acid. Removal of DMT from the support-bound oligonucleotide is generally performed with DCA (e.g. about 3 to about 10 percent DCA (v/v) in a suitable solvent. Removal of oligonucleotide after cleavage from the support is generally performed with acetic acid.

As described herein, oligonucleotides can be prepared as chimeras with other oligomeric moieties. In the context of this invention, the term "oligomeric compound" refers to a polymeric structure capable of hybridizing a region of a nucleic acid molecule, and an "oligomeric moiety" a portion of such an oligomeric compound. Oligomeric compounds include oligonucleotides, oligonucleosides, oligonucleotide analogs, modified oligonucleotides and oligonucleotide mimetics. Oligomeric compounds can be linear or circular, and may include branching. They can be single stranded or double stranded, and when double stranded, may include overhangs. In general an oligomeric compound comprises a backbone of linked monomeric subunits where each linked monomeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras. As is known in the art, a nucleoside is a base-sugar combination. The base portion of the nucleoside is normally a heterocyclic base moiety. The two most common classes of such heterocyclic bases are purines and pyrimidines. In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Synthetic schemes for the synthesis of the substitute internucleoside linkages described above are disclosed in: U.S. Pat. Nos. 5,466,677; 5,034,506; 5,124,047; 5,278,302; 5,321,131; 5,519,126; 4,469,863; 5,455,233; 5,214,134; 5,470,967; 5,434,257. Additional background information relating to internucleoside linkages can be found in: WO 91/08213; WO 90/15065; WO 91/15500; WO 92/20822; WO 92/20823; WO 91/15500; WO 89/12060; EP 216860; PCT/US 92/04294; PCT/US 90/03138; PCT/US 91/06855; PCT/US 92/03385; PCT/US 91/03680; U.S. application Ser. Nos. 07/990,848; 07/892,902, now U.S. Pat. No. 5,817,781, issued on Oct. 6, 1998; Ser. Nos. 07/806,710; 07/763,130, now U.S. Pat. No. 5,596,086, issued on Jan. 21, 1997; Ser. No. 07/690,786, now U.S. Pat. No. 5,264,562, issued on Nov. 23, 1993; Stirchak, E. P., et al., Nucleic Acid Res., 1989, 17, 6129-6141; Hewitt, J. M., et al., 1992, 11, 1661-1666; Sood, A., et al., J. Am. Chem. Soc., 1990, 112, 9000-9001; Vaseur, J. J. et al., J. Amer. Chem. Soc., 1992, 114, 4006-4007; Musichi, B., et al., J. Org. Chem., 1990, 55, 4231-4233; Reynolds, R. C., et al., J. Org. Chem., 1992, 57, 2983-2985; Mertes, M. P., et al., J. Med. Chem., 1969, 12, 154-157; Mungall, W. S., et al., J. Org. Chem., 1977, 42, 703-706; Stirchak, E. P., et al., J. Org. Chem., 1987, 52, 4202-4206; Coull, J. M., et al., Tet. Lett., 1987, 28, 745; and Wang, H., et al., Tet. Lett., 1991, 32, 7385-7388.

Phosphoramidites used in the synthesis of oligonucleotides are available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). These commercial sources sell high purity phosphoramidites generally having a purity of better than 98%. Those not offering an across the board purity for all amidites sold will in most cases include an assay with each lot purchased giving at least the purity of the particular phosphoramidite purchased. Commercially available phosphoramidites are prepared for the most part for automated DNA synthesis and as such are prepared for immediate use for synthesizing desired sequences of oligonucleotides. Phosphoramidites may be prepared by methods disclosed by e.g. Caruthers et al. (U.S. Pat. Nos. 4,415,732; 4,458,066; 4,500,707; 4,668,777; 4,973,679; and 5,132,418) and Köster et al. (U.S. Pat. No. RE 34,069).

Double stranded oligonucleotides, such as double-stranded RNA, may be manufactured according to methods according to the present invention, as described herein. In the case of RNA synthesis, it is necessary to protect the 2'-OH of the amidite reagent with a suitable removable protecting groups. Suitable protecting groups for 2'-OH are described in U.S. Pat. Nos. 6,008,400, 6,111,086 and 5,889,136. A particularly suitable 2'-protecting group for RNA synthesis is the ACE protecting group as described in U.S. Pat. No. 6,111,086. In some embodiments, it is considered advantageous to use a different 5'-protecting group for amidites used in RNA synthesis. Suitable 5'-protecting groups are set forth in U.S. Pat. No. 6,008,400. A particularly suitable 5'-protecting group is the trimethylsilyloxy (TMSO) group as taught in U.S. Pat. No. 6,008,400. See especially example 1, columns 10-13. The separate strands of the double stranded RNA may be separately synthesized and then annealed to form the double stranded (duplex) oligonucleotide.

Oligonucleotide Use

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RnA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

RNAse H-Dependent Antisense

One method for inhibiting specific gene expression involves using oligonucleotides or oligonucleotide analogs as "antisense" agents. Antisense technology involves directing oligonucleotides, or analogs thereof, to a specific, target messenger RNA (mRNA) sequence. The interaction of exogenous "antisense" molecules and endogenous mRNA modulates transcription by a variety of pathways. Such pathways include transcription arrest, RNAse H recruitment, and RNAi (e.g. siRNA). Antisense technology permits modulation of specific protein activity in a relatively predictable manner.

EXAMPLES

The present invention may be further understood with reference to the following, non-limiting, illustrative examples, which may be carried out by methods generally described hereinabove.

Example 1

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 7 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 2

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 15 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 3

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 20 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 4

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 80° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 5

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 85° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 6

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (250 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 7

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (110 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 8

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (15 g), acetoxystyrene (10 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 9

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (20 g), benzoylperoxide (4 g), isooctane (90 g), 2-ethylhexanol (200 g) are added to the reaction vessel. The mixture is stirred at a fixed speed (250 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 10

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (40 g), 2-ethylhexanol (200 g) are added to the reaction vessel. The mixture is stirred at a fixed speed (250 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 11

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (350 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 12

Deionized water (1500 mL) and polyvinyl alcohol (40 g) are placed in the reaction vessel (2 L) equipped with a mechanical stirrer, condenser and nitrogen inlet. The reaction is kept under nitrogen atmosphere throughout the entire polymerization process. An organic solution composed of styrene (190 g), 55%-divinylbenzene (45%-ethylstyrene) (30 g), acetoxystyrene (10 g), benzoylperoxide (4 g), isooctane (90 g), 2-ethylhexanol (200 g) are added to the reaction vessel. The mixture is stirred at a fixed speed (450 rpm) to produce the desired bead size distribution. Then the reactor is heated at 75° C. After 12 h, the motor is stopped and the beads formed are filtered and washed with deionized water and acetone. The beads are dispersed in acetone and then sieved and dried under vacuum. Deionized water (300 mL), ethanol (1000 mL) and dried beads are placed in a reaction vessel (2 L) equipped with a mechanical stirrer (200 rpm) and condenser. Then the reactor is heated at 70° C. After 12 h, the motor is stopped and the beads formed are filtered and washed with deionized water and acetone. The beads are dispersed in acetone and then sieved and dried under vacuum.

Example 13

Loading of 5'-O-DMT thymidine-3'-O-succinate to solid support

Loading of the protected nucleoside is performed under the standard conditions using solid support obtained from experiment 1. Solid support, Hunig's base (12 equiv), HBTU activator (4 equiv), the DMT T nucleoside succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 14

Loading of 5'-O-DMT-N4-benzoyl-2'-deoxycytidine-3'-O-succinate to solid support

Loading of the protected nucleoside is performed under the standard conditions using solid support obtained from experiment 1. Solid support, Hunig's base (12 equiv), HBTU activator (4 equiv), 5'-O-DMT-N4-benzoyl-2'-deoxycytidine-3'-O-succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 15

Loading of 5'-O-DMT-N6-benzoyl-2'-deoxyadenosine-3'-O-succinate to solid support Loading of the protected nucleoside is performed under the standard conditions using solid support obtained from experiment 1. Solid support, Hunig's base (12 equiv), HBTU activator (4 equiv), 5'-O-DMT-N6-benzoyl-2'-deoxyadenosine-3'-O-succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 16

Loading of 5'-O-DMT-N2-isobutyryl-2'-deoxyguanosine-3'-O-succinate to solid support Loading of the protected nucleoside is performed under the standard conditions using solid support obtained from experiment 1. Solid support, Hunig's base (12 equiv), HBTU activator (4 equiv), 5'-O-DMT-N2-isobutyryl-2'-deoxyguanosine-3'-O-succinate as the triethyl ammonium salt (2.0 equiv) are taken in a round bottom flask and closed and shaken mechanically at room temperature for 10 hours. The support is then washed with a acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 17

Loading of 5'-O-DMT-2'-O-methoxyethyl-5-methyluridine-3'-O-succinate to solid support Loading of the protected nucleoside is performed under the standard conditions using solid support obtained from experiment 1. Solid support, Hunig's base (12 equiv), HBTU activator (4 equiv), 5'-O-DMT-2'-O-methoxyethyl-5-methyluridine-3'-O-succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 18

Loading of 5'-O-DMT-N4-benzoyl-2'-O-methoxyethylcytidine-3'-O-succinate to solid support Loading of the protected nucleoside is performed under the standard conditions using solid support obtained from experiment 1. Solid support, Hunig's base (12 equiv), HBTU activator (4 equiv), 5'-O-DMT-N4-benzoyl-2'-O-methoxyethylcytidine-3'-O-succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 19

Loading of 5'-O-DMT-N6-benzoyl-2'-methoxyethyladenosine-3'-O-succinate to solid support Loading of the protected nucleoside is performed under the standard conditions using solid support obtained from experiment 1. Solid support, Hunig's base (12 equiv), HBTU activator (4 equiv), 5'-O-DMT-N6-benzoyl-2'-O-methoxyethyladenosine-3'-O-succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 20

Loading of 5'-O-DMT-N2-isobutyryl-2'-O-methoxyethylguanosine-3'-O-succinate to solid support Loading of the protected nucleoside is performed under the standard conditions using solid support obtained from experiment 1. Solid support, Hunig's base (12 equiv), HBTU activator (4 equiv), 5'-O-DMT-N2-isobutyryl-2'-O-methoxyethylguanosine-3'-O-succinate as the triethyl ammonium salt (2.0 equiv) are taken in a round bottom flask and closed and shaken mechanically at room temperature for 10 hours. The support is then washed with acetonitrile (100 ml) and dried. Then a mixture of Cap A and Cap B solution used for oligomerization (20 ml each) are added to the solid support followed by a catalytic amount of 4-dimethylaminopyridine and shaken overnight mechanically. The support is washed with acetonitrile (200 ml), methanol (100 ml) and finally with anhydrous ether (200 ml). The support is finally dried thoroughly and stored.

Example 21

Synthesis of fully-modified 5'-d(TCC-CGC-CTG-TGA-CAT-GCA-TT)-3' phosphorothioate 20-mer (SEQ ID NO: 1)

The synthesis of above sequence is performed on a Amersham Biosciences Akta 100 DNA/RNA Synthesizer on approximately 420 micromole scale using the cyanoethyl phosphoramidites and DMT thymidine-derivatized solid support prepared as above. Detritylation is performed using 10% dichloroacetic acid in toluene (volume/volume). Sulfurization is performed using a 0.2 M solution of phenylacetyl disulfide in acetonitrile: 3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 22

Synthesis of fully-modified 5'-d(GTT-CTC-GCT-GGT-GAG-TTT-CA)-3' phosphorothioate 20-mer (SEQ ID NO: 2)

The synthesis of above sequence is performed on a Amersham Biosciences Akta 100 DNA/RNA Synthesizer on approximately 420 micromole scale using the cyanoethyl phosphoramidites and DMT N6-benzoyl-2'-deoxyadenosine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 23

Synthesis of fully-modified 5'-d(GCC-CAA-GCT-GGC-ATC-CGT-CA)-3' phosphorothioate 20-mer (SEQ ID NO: 3)

The synthesis of above sequence is performed on a Amersham Biosciences Akta 100 DNA/RNA Synthesizer on approximately 420 micromole scale using the cyanoethyl phosphoramidites and DMT N6-benzoyl-2'-deoxyadenosine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 24

Synthesis of fully-modified 5'-d(TCC-GTC-ATC-GCT-CCT-CAG-GG)-3' phosphorothioate 20-mer (SEQ ID NO: 4)

The synthesis of above sequence is performed on a Amersham Biosciences Akta 100 DNA/RNA Synthesizer on approximately 420 micromole scale using the cyanoethyl phosphoramidites and DMT N2-isobutyryl-2'-deoxyguanosine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 25

Synthesis of fully-modified 5'-d(GTT-CTC-GCT-GGT-GAG-TTT-CA)-3' phosphorothioate 20-mer (SEQ ID NO: 2)

The synthesis of above sequence is performed on a Amersham Biosciences Akta 100 DNA/RNA Synthesizer on approximately 420 micromole scale using the cyanoethyl phosphoramidites and DMT N6-benzoyl-2'-deoxyadenosine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 26

Synthesis of fully-modified 5'-[2'-O-methoxyethyl-(TGTG]-d(CTA-TTC-TGT-G-)-[2'-O-methoxyethyl-(AATT]-3' phosphorothioate 18-mer (SEQ ID NO: 5)

The synthesis of above sequence is performed on a Amersham Biosciences Akta 100 DNA/RNA Synthesizer on approximately 420 micromole scale using the cyanoethyl phosphoramidites and 5'-O-DMT-2'-O-methoxyethyl-5-methyluridine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 27

Synthesis of fully-modified 5'-[2'-O-methoxyethyl-(CAGC]-d(AGC-AGA-GTC-TTC-A-)-[2'-O-methoxyethyl-(TCAT]-3' phosphorothioate 21-mer (SEQ ID NO: 6)

The synthesis of above sequence is performed on a Amersham Biosciences Akta 100 DNA/RNA Synthesizer on approximately 420 micromole scale using the cyanoethyl phosphoramidites and 5'-O-DMT-2'-O-methoxyethyl-5-methyluridine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 28

Synthesis of fully-modified 5'-[2'-O-methoxyethyl-(GCTCC]-d(TTC-CAC-TGA-T)-[2'-O-methoxyethyl-(CCTGC]-3' phosphorothioate 20-mer (SEQ ID NO: 7)

The synthesis of above sequence is performed on a Amersham Biosciences Akta 100 DNA/RNA Synthesizer on approximately 420 micromole scale using the cyanoethyl phosphoramidites and 5'-O-DMT-2'-O-methoxyethyl-5-methylcytidine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 29

Synthesis of fully-modified 5'-[2'-O-methoxyethyl-(GCTCC]-d(TTC-CAC-TGA-T)-[2'-O-methoxyethyl-(CCTGC]-3' phosphorothioate 20-mer (SEQ ID NO: 7)

The synthesis of above sequence is performed on a Amersham Biosciences Akta 100 DNA/RNA Synthesizer on approximately 420 micromole scale using the cyanoethyl phosphoramidites and 5'-O-DMT-2'-O-methoxyethyl-5-methylcytidine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 30

The synthesis of fully-modified 5'-[2'-O-methoxyethyl-(GCCTC]-d(AGT-CTG-CTT-C)-[2'-O-methoxyethyl-(GCACC]-3' phosphorothioate 20-mer (SEQ ID NO: 8)

The synthesis of above sequence is performed on a Amersham Biosciences Akta 100 DNA/RNA Synthesizer on approximately 420 micromole scale using the cyanoethyl phosphoramidites and 5'-O-DMT-2'-O-methoxyethyl-5-methylcytidine-derivatized solid support prepared as above. Detritylation is performed using 10% dichloroacetic acid in toluene (volume/volume). Sulfurization is performed using a 0.2 M solution of phenylacetyl disulfide in acetonitrile:3-picoline (1:1 v/v) for 2 minutes. At the end of synthesis, the support is washed with acetonitrile, cleaved, deprotected using ammonium hydroxide at 55 deg C. for 12 hours. The crude material is purified in the usual manner to afford the desired phosphorothioate oligonucleotide.

Example 31

Synthesis of 5'-d(TCC-CGC-CTG-TGA-CAT-GCA-TT)-3' phosphate diester 20-mer (SEQ ID NO: 1)

The synthesis of above sequence is performed on a Amersham Biosciences Akta 100 DNA/RNA Synthesizer on approximately 420 micromole scale using the cyanoethyl phosphoramidites and DMT thymidine-derivatized solid support prepared as above. Detritylation is performed using 10% dichloroacetic acid in toluene (volume/volume). Oxidation is performed using standard iodine solution for 2 minutes. At the end of synthesis, the support is washed with acetonitrile, cleaved, deprotected using ammonium hydroxide at 55 deg C. for 12 hours. The crude material is purified in the usual manner to afford the desired phosphate oligonucleotide.

Example 32

Synthesis of 5'-d(GTT-CTC-GCT-GGT-GAG-TTT-CA)-3' phosphate diester 20-mer (SEQ ID NO: 2)

The synthesis of above sequence is performed on a Amersham Biosciences Akta 100 DNA/RNA Synthesizer on approximately 420 micromole scale using the cyanoethyl phosphoramidites and DMT N6-benzoyl-2'-deoxyadenosine-derivatized solid support prepared as above. Detritylation is performed using 10% dichloroacetic acid in toluene (volume/volume). Oxidation is preformed using standard iodine solution for 2 minutes. At the end of synthesis, the support is washed with acetonitrile, cleaved, deprotected using ammonium hydroxide at 55 deg C. for 12 hours. The crude material is purified in the usual manner to afford the desired phosphate oligonucleotide.

Example 33

Synthesis of 5'-d(GCC-CAA-GCT-GGC-ATC-CGT-CA)-3' phosphate diester 20-mer (SEQ ID NO: 3)

The synthesis of above sequence is performed on a Amersham Biosciences Akta 100 DNA/RNA Synthesizer on approximately 420 micromole scale using the cyanoethyl phosphoramidites and DMT N6-benzoyl-2'-deoxyadenosine-derivatized solid support prepared as above. Detritylation is performed using 10% dichloroacetic acid in toluene (volume/volume). Oxidation is performed using standard iodine solution for 2 minutes. At the end of synthesis, the support is washed with acetonitrile, cleaved, deprotected using ammonium hydroxide at 55 deg C. for 12 hours. The crude material is purified in the usual manner to afford the desired phosphate oligonucleotide.

Example 34

Synthesis of 5'-d(TCC-GTC-ATC-GCT-CCT-CAG-GG)-3' phosphate diester 20-mer (SEQ ID NO: 4)

The synthesis of above sequence is performed on a Amersham Biosciences Akta 100 DNA/RNA Synthesizer on approximately 420 micromole scale using the cyanoethyl phosphoramidites and DMT N2-isobutyryl-2'-deoxyguanosine-derivatized solid support prepared as above. Detritylation is performed using 10% dichloroacetic acid in toluene (volume/volume). Oxidation is performed using standard iodine solution for 2 minutes. At the end of synthesis, the support is washed with acetonitrile, cleaved, deprotected using ammonium hydroxide at 55 deg C. for 12 hours. The crude material is purified in the usual manner to afford the desired phosphate oligonucleotide.

Example 35

Synthesis of 5'-d(GTT-CTC-GCT-GGT-GAG-TTT-CA)-3' phosphate 20-mer (SEQ ID NO: 2)

The synthesis of above sequence is performed on a Amersham Biosciences Akta 100 DNA/RNA Synthesizer on approximately 420 micromole scale using the cyanoethyl phosphoramidites and DMT N6-benzoyl-2'-deoxyadenosine-derivatized solid support prepared as above. Detritylation is performed using 10% dichloroacetic acid in toluene (volume/volume). Oxidation is performed using standard iodine solution for 2 minutes. At the end of synthesis, the support is washed with acetonitrile, cleaved, deprotected using ammonium hydroxide at 55 deg C. for 12 hours. The crude material is purified in the usual manner to afford the desired phosphate oligonucleotide.

Example 36

General Procedure for Synthesis of Oligonucleotides

A 2.2 mM synthesis is performed according to the following procedure:
1. Discharge 11.0 g of 200 μm loaded support into a 35 mm flow-through column;
2. Add approximately 150 mL of toluene to the column and allow the support to swell for several minutes. The swelled support should measure approximately 5.2 cm from the columns bottom plate to the top of the support bed.
3. Lower the columns top net adapter to approximately 7.2 cm, creating a 2 cm gap between the support bed and the columns top plate.
4. Secure column locking mechanism.
5. Perform solid phase oligonucleotides synthesis using nucleoside phosphoramidites to produce an oligonucleotide having phosphodiester, phosphorothioate, or phosphorodithioate internucleoside linkages.

The synthesis of step 5 can include the attachment of a first nucleoside to the support via a linker (for example a unilinker) using standard reagents, if the support is not previously derivatized to contain such a first synthon. Alternatively, if the support has been previously derivatized, the derivatized support is loaded on the column as described above, the synthesis proceeds with the addition of phosphoramidites synthons. In addition, if the support (derivatized or not derivatized) has been previously swelled before loading onto the column, then the swelled support is loaded to allow for the aforementioned 2 cm gap.

Example 37

Synthesis of Polymeric Beads

In order to determine the effects of the various experimental parameters on the properties of the beads, several beads were produced under different preparative conditions, and their physical properties examined. The results are summarized in the table below.

| Experimental parameter | Experiment number | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Water (g) | 1500 | 1500 | 1500 | 1500 | 1500 | 1500 | 1500 | 1500 | 1500 | 1500 | 1500 | 1500 |
| Polyvinyl alcohol (g) | 40 | 40 | 40 | 40 | 40 | 40 | 40 | 40 | 40 | 40 | 40 | 40 |
| Styrene (g) | 190 | 190 | 190 | 190 | 190 | 250 | 110 | 190 | 190 | 190 | 190 | 190 |
| Ethylstyrene (g) | 13.5 | 13.5 | 13.5 | 13.5 | 13.5 | 13.5 | 13.5 | 6.75 | 13.5 | 13.5 | 13.5 | 13.5 |
| DVB (g) | 16.5 | 16.5 | 16.5 | 16.5 | 16.5 | 16.5 | 16.5 | 8.25 | 16.5 | 16.5 | 16.5 | 16.5 |
| Acetoxystyrene (g) | 10 | 10 | 10 | 10 | 10 | 10 | 10 | 10 | 20 | 10 | 10 | 10 |
| BPO (g) | 4 | 4 | 4 | 4 | 4 | 4 | 4 | 4 | 4 | 4 | 4 | 4 |
| Isooctane (g) | 90 | 90 | 90 | 90 | 90 | 90 | 90 | 90 | 90 | 40 | 90 | 90 |
| 2-ethylhexanol (g) | 200 | 200 | 200 | 200 | 200 | 200 | 200 | 200 | 200 | 200 | 200 | 200 |
| Stir (rpm) | 250 | 250 | 250 | 250 | 250 | 250 | 250 | 250 | 250 | 250 | 350 | 450 |
| Temp (° C.) | 75 | 75 | 75 | 80 | 85 | 75 | 75 | 75 | 75 | 75 | 75 | 75 |
| Time (h) | 7 | 15 | 20 | 7 | 7 | 7 | 7 | 7 | 7 | 7 | 7 | 7 |
| Monomer/Tot monomer percentages | | | | | | | | | | | | |
| Styrene + Ethylstyrene | 88 | 88 | 88 | 88 | 88 | 91 | 82 | 92 | 85 | 88 | 88 | 88 |
| DVB | 7 | 7 | 7 | 7 | 7 | 6 | 11 | 4 | 7 | 7 | 7 | 7 |
| Acetoxystyrene | 4 | 4 | 4 | 4 | 4 | 3 | 7 | 5 | 8 | 4 | 4 | 4 |
| Organic solvent percentages | | | | | | | | | | | | |
| Isooctane | 31 | 31 | 31 | 31 | 31 | 31 | 31 | 31 | 31 | 17 | 31 | 31 |
| 2-ethylhexanol | 69 | 69 | 69 | 69 | 69 | 69 | 69 | 69 | 69 | 83 | 69 | 69 |
| Organic phase percantages | | | | | | | | | | | | |
| organic solvent | 56 | 56 | 56 | 56 | 56 | 50 | 66 | 57 | 55 | 51 | 56 | 56 |
| tot monomers | 44 | 44 | 44 | 44 | 44 | 50 | 34 | 43 | 45 | 49 | 44 | 44 |
| Organic/Aqueous percentages | | | | | | | | | | | | |
| organic phase | 25 | 25 | 25 | 25 | 25 | 27 | 22 | 25 | 26 | 23 | 25 | 25 |
| aqueous phase | 75 | 75 | 75 | 75 | 75 | 73 | 78 | 75 | 74 | 77 | 75 | 75 |
| Bead property | | | | | | | | | | | | |
| [1]Average particle size (μm) | 80 | 80 | 81 | 80 | 78 | 101 | 72 | 78 | 80 | 75 | 62 | 38 |
| [2]Average pore size (nm) | 27 | 27 | 29 | 25 | 21 | 19 | 110 | 10 | 23 | 21 | 34 | 41 |
| [3]Specific surface area ($m^2/g$) | 51 | 51 | 50 | 55 | 61 | 37 | 28 | 21 | 48 | 43 | 62 | 70 |

[1]Measured by laser scattering
[2]Measured by mercury porosimetry
[3]Measured by BET method Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

It is intended that each of the patents, applications, and printed publications including books mentioned in this patent document be hereby incorporated by reference in their entirety.

What is claimed is:

1. A process of making a polymeric bead comprising:
   (a) providing an organic phase; and
   (b) contacting said organic phase with an aqueous phase, under conditions of time, temperature and pressure effective to form the polymeric bead, wherein
   said organic phase comprises the olefin monomer styrene, a cross-linking monomer, a functionalizing monomer that is an acetoxystyrene, an initiator, an organic solvent;
   wherein said organic solvent comprises one or more liquid hydrocarbons; and/or an alcohol having from five to twelve carbon atoms;
   said aqueous phase comprises water and a dispersing reagent;
   and wherein
   the percentage by weight of the olefin monomer styrene initially present in total monomers is from about 60% to about 96%;
   the percentage by weight of cross-linking monomer initially present in total monomers is from about 3% to 9.9%;
   the percentage by weight of the functionalizing monomer initially present in total monomers is from about 1% to about 20%;
   the percentage by weight of monomers initially present in the organic phase is from about 33% to about 67%;
   the percentage by weight of the organic solvent initially present in the organic phase is from about 33% to about 67%;
   the percentage by weight of liquid hydrocarbon present in the organic solvent is from about 0% to about 80%;
   the percentage by weight of an alcohol having from five to twelve carbon atoms initially present in the organic solvent is from about 20% to about 100%; and
   the percentage by weight of the dispersing reagent initially present in the aqueous phase is from about 0.01% to about 20%.

2. The process of claim 1, wherein:
   the percentage by weight of the olefin monomer styrene initially present in total monomers is from about 75% to about 94%;
   the percentage by weight of cross-linking monomer initially present in total monomers is from about 4% to 9.9%;
   the percentage by weight of the functionalizing monomer initially present in total monomers is from about 2% to about 10%;
   the percentage by weight of monomers initially present in the organic phase is from about 35% to about 60%;
   the percentage by weight of the organic solvent initially present in the organic phase is from about 40% to about 65%;
   the percentage by weight of hydrocarbon present in the organic solvent is from about 5% to about 70%; and
   the percentage by weight of an alcohol having from five to twelve carbon atoms initially present in the organic solvent is from about 30% to about 95%.

3. The process of claim 1 wherein:
   the percentage by weight of the olefin monomer styrene initially present in total monomers is from about 82% to about 91.5%;
   the percentage by weight of cross-linking monomer initially present in total monomers is from about 5.5% to 9.9%;

the percentage by weight of the functionalizing monomer initially present in total monomers is from about 3% to about 8%;

the percentage by weight of monomers initially present in the organic phase is from about 40% to about 50%;

the percentage by weight of the organic solvent initially present in the organic phase is from about 50% to about 60%;

the percentage by weight of liquid hydrocarbon present in the organic solvent is from about 10% to about 60%; and the percentage by weight of an alcohol having from five to twelve carbon atoms initially present in the organic solvent is from about 40% to about 90%.

4. The process of claim 1 wherein the olefin monomers comprise one or more aryl-vinyl compounds.

5. The process of claim 1 wherein the cross-linking monomer is an olefinic cross-linking monomer having two unconjugated vinyl groups.

6. The process of claim 1 wherein the cross-linking monomer is an olefinic cross-linking monomer having two unconjugated vinyl groups attached to an aromatic moiety; wherein the aromatic moiety is a five or six member aromatic ring.

7. The process of claim 1, wherein the cross-linking monomer is divinylbenzene.

8. The process of claim 1, wherein the functionalizing monomer is 4-acetoxystrene.

9. The process of claim 1, wherein the initiator is a stabilized peroxide or azo compound.

10. The process of claim 9, wherein the stabilized peroxide comprises benzoylperoxide.

11. The process of claim 1, wherein the organic solvent comprises one or more liquid alkanes, benzene, toluene, xylenes and/or an alcohol having from five to twelve carbon atoms.

12. The process of claim 1, wherein the organic solvent comprises one or more octanes, and/or an alcohol having five to twelve carbon atoms.

13. The process of claim 1, wherein the organic solvent comprises isooctane, and/or 2-ethylhexanol.

14. The process of claim 1, wherein the dispersing reagent comprises a polyalcohol.

15. The process of claim 1, wherein the dispersing reagent comprises polyvinyalcohol.

16. The process of claim 1, wherein the organic phase and aqueous phase are heated to a temperature of about 25° C. to about 95° C.

17. The process of claim 1, wherein the organic phase and aqueous phase are heated to a temperature of about 70° C. to about 85° C.

18. The process of claim 1, wherein the organic phase and the aqueous phase are heated to a temperature of about 75° C. to about 80° C.

19. A polymeric bead formed by the process of claim 1.

20. The polymeric bead of claim 19, wherein said bead has a loading capability of from about 100 μmole per gram of bead to about 350 μmole per gram of bead.

21. The polymeric bead of claim 19, wherein said bead has an average particle size of 10-300 μm.

22. The polymeric bead of claim 19, wherein said bead has an average pore size of 10-100 nm.

23. The polymeric bead of claim 19, wherein said bead has a specific surface area of 10-100 m$^2$/g.

24. A compound of Formula I:

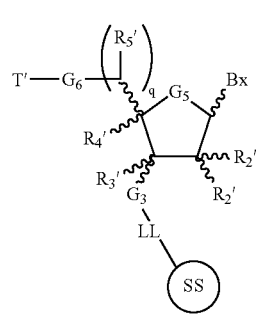

I wherein:
$G_3$ is O, S, $CH_2$, or NH;
$G_5$ is O, S, $CH_2$, CFH, $CF_2$, or —CH═CH—;
$G_6$ is O, S, $CH_2$, or NH;
each $R_2'$ is H, OH, O-rg, wherein rg is a removable protecting group, a 2'-substituent, or together with $R_4'$ forms a bridge;
each $R_3'$ is H or a substituent;
each $R_4'$ is H, a substituent or together with $R_2'$ forms a bridge;
q is 0 or 1;
$R_5'$ is H, or a substituent;
Bx is a nucleobase;
T' is H or a removable protecting group;
LL is a linking moiety; and
SS is a bead of claim 19.

25. A compound of Formula II:

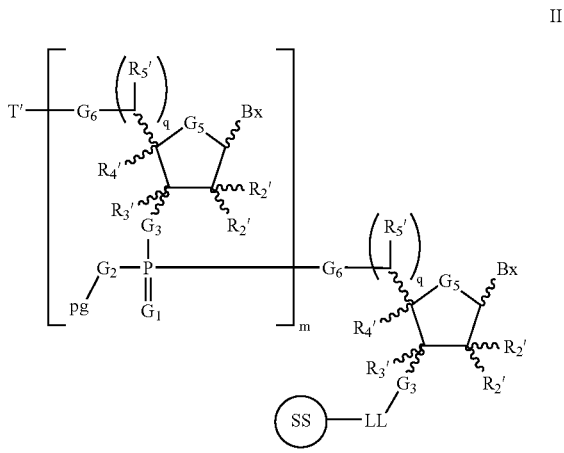

II wherein:
m is an integer from 0 to about 100;
each $G_1$ is O or S;
each $G_2$ is OH or SH;
each $G_3$ is O, S, $CH_2$, or NH;
each $G_5$ is O, S, $CH_2$, CFH, $CF_2$, or —CH═CH—;

each $R_2'$ is H, OH, O-rg, wherein rg is a removable protecting group, a 2'-substituent, or together with $R_4'$ forms a bridge;

each $R_3'$ is H or a substituent;

each $R_4'$ is H, a substituent or together with $R_2'$ forms a bridge;

each q is 0 or 1;

each $R_5'$ is H, or a substituent;

each $G_6$ is independently O, S, $CH_2$ or NH;

each Bx is a nucleobase;

pg is a removable phosphorous protecting group;

T' is a removable protecting group;

LL is a linking moiety; and

SS is a bead of claim 19.

* * * * *

```
                              SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
tcccgcctgt gacatgcatt                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
gttctcgctg gtgagtttca                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gcccaagctg gcatccgtca                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tccgtcatcg ctcctcaggg                                                   20

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
tgtgctattc tgtgaatt                                                     18

<210> SEQ ID NO 6
<211> LENGTH: 21
<212> TYPE: DNA
<213> ORGANISM: Artificial Sequence
```

-continued

```
<220> FEATURE:
<223> OTHER INFORMATION: Synthetic oligonucleotide

<400> SEQUENCE: 6
cagcagcaga gtcttcatca t                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gctccttcca ctgatcctgc                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gcctcagtct gcttcgcacc                                                20
```